(12) United States Patent
Melodia et al.

(10) Patent No.: US 11,115,475 B2
(45) Date of Patent: Sep. 7, 2021

(54) SOFTWARE-DEFINED IMPLANTABLE ULTRASONIC DEVICE FOR USE IN THE INTERNET OF MEDICAL THINGS

(71) Applicant: Northeastern University, Boston, MA (US)

(72) Inventors: Tommaso Melodia, Newton, MA (US); Giuseppe Enrico Santagati, Cambridge, MA (US)

(73) Assignee: Northeastern University, Boston, MA (US)

( * ) Notice: Subject to any disclaimer, the term of this patent is extended or adjusted under 35 U.S.C. 154(b) by 137 days.

(21) Appl. No.: 15/679,717

(22) Filed: Aug. 17, 2017

(65) Prior Publication Data

US 2018/0027077 A1   Jan. 25, 2018

Related U.S. Application Data

(63) Continuation-in-part of application No. 15/546,423, filed as application No. PCT/US2016/014860 on Jan. 26, 2016, now Pat. No. 10,849,503.

(Continued)

(51) Int. Cl.
*A61B 5/00* (2006.01)
*H04B 11/00* (2006.01)
(Continued)

(52) U.S. Cl.
CPC ............ *H04L 67/12* (2013.01); *A61B 5/0015* (2013.01); *A61B 5/0022* (2013.01); *A61B 5/0028* (2013.01); *A61B 5/0031* (2013.01); *G16H 40/67* (2018.01); *H04B 1/385* (2013.01); *H04B 11/00* (2013.01); *H04B 13/005* (2013.01); *H04W 4/38* (2018.02); *H04W 4/70* (2018.02); *H04W 4/80* (2018.02); *A61B 5/0077* (2013.01); *A61B 5/024* (2013.01); *A61B 5/0215* (2013.01); *A61B 5/08* (2013.01); *A61B 5/14532* (2013.01); *A61B 5/14539* (2013.01); *A61B 5/14542* (2013.01); *A61B 5/14546* (2013.01); *A61B 5/283* (2021.01); *A61B 5/291* (2021.01); *A61B 5/389* (2021.01); *A61B 5/4806* (2013.01); *A61B 5/4845* (2013.01); *A61B 5/6846* (2013.01); *A61B 2562/0219* (2013.01); *H04L 61/6059* (2013.01); *H04W 52/0209* (2013.01); *Y02D 30/70* (2020.08)

(58) Field of Classification Search
CPC .... H04B 11/00; G08B 21/0453; G16H 50/20; H04M 1/6066; H04W 4/08; H04W 52/0219; H04W 52/0251; H04W 8/22
See application file for complete search history.

(56) References Cited

U.S. PATENT DOCUMENTS 6,695,885 B2   2/2004   Schulman et al.
7,733,224 B2   6/2010   Tran
(Continued)

*Primary Examiner* — Curtis A Kuntz
*Assistant Examiner* — Jerold B Murphy
(74) *Attorney, Agent, or Firm* — Verrill Dana, LLP

(57) ABSTRACT

Implantable and wearable devices and system for transmitting signals ultrasonically through biological tissue are implemented based on an Internet of Medical Things (IoMT) platform software and hardware architecture. The devices are size-, energy-, and resource-constrained and implement ultrasonic communication protocols and communicate with each other through ultrasound.

21 Claims, 15 Drawing Sheets

Related U.S. Application Data

(60) Provisional application No. 62/376,027, filed on Aug. 17, 2016, provisional application No. 62/107,737, filed on Jan. 26, 2015.

(51) Int. Cl.

| | |
|---|---|
| *H04B 13/00* | (2006.01) |
| *H04L 29/08* | (2006.01) |
| *H04B 1/3827* | (2015.01) |
| *H04W 4/80* | (2018.01) |
| *H04W 4/38* | (2018.01) |
| *G16H 40/67* | (2018.01) |
| *H04W 4/70* | (2018.01) |
| *H04L 29/12* | (2006.01) |
| *H04W 52/02* | (2009.01) |
| *A61B 5/145* | (2006.01) |
| *A61B 5/024* | (2006.01) |
| *A61B 5/0215* | (2006.01) |
| *A61B 5/08* | (2006.01) |
| *A61B 5/283* | (2021.01) |
| *A61B 5/291* | (2021.01) |
| *A61B 5/389* | (2021.01) |

(56) References Cited

U.S. PATENT DOCUMENTS

| | | | | |
|---|---|---|---|---|
| 8,301,232 | B2 * | 10/2012 | Albert | A61B 5/0006 |
| | | | | 600/509 |
| 8,509,882 | B2 * | 8/2013 | Albert | A61B 5/0404 |
| | | | | 600/509 |
| 9,451,340 | B2 * | 9/2016 | Duesterhoft | G06F 19/00 |
| 9,514,066 | B1 * | 12/2016 | Diaz | G06F 13/20 |
| 2004/0015079 | A1 | 1/2004 | Berger et al. | |
| 2004/0202339 | A1 * | 10/2004 | O'Brien, Jr. | H04B 13/005 |
| | | | | 381/312 |
| 2006/0224048 | A1 | 10/2006 | Devaul et al. | |
| 2010/0298669 | A1 * | 11/2010 | Ida | A61B 5/0002 |
| | | | | 600/302 |
| 2013/0197320 | A1 * | 8/2013 | Albert | A61B 5/02055 |
| | | | | 600/301 |
| 2013/0274563 | A1 * | 10/2013 | Duesterhoft | A61B 5/4848 |
| | | | | 600/301 |
| 2014/0128754 | A1 * | 5/2014 | Luna | A61B 5/746 |
| | | | | 600/500 |
| 2014/0206976 | A1 | 7/2014 | Thompson et al. | |
| 2015/0018660 | A1 * | 1/2015 | Thomson | A61B 5/0404 |
| | | | | 600/393 |
| 2015/0261415 | A1 * | 9/2015 | Lee | H04L 41/0803 |
| | | | | 715/716 |
| 2016/0174158 | A1 * | 6/2016 | Vance | H04W 52/0219 |
| | | | | 455/418 |
| 2017/0284859 | A1 * | 10/2017 | Bauer | G01N 29/024 |
| 2017/0284920 | A1 * | 10/2017 | Bauer | G01N 29/024 |

\* cited by examiner

SOFTWARE-DEFINED IMPLANTABLE ULTRASONIC DEVICE FOR USE IN THE INTERNET OF MEDICAL THINGS

CROSS REFERENCE TO RELATED APPLICATIONS

This application claims priority under 35 U.S.C. § 119(e) of U.S. Provisional Application No. 62/376,027, filed on Aug. 17, 2016, entitled "Software-Defined Implantable Ultrasonic Device for Use in the Internet of Medical Things," the disclosure of which is hereby incorporated by reference.

This application claims priority under 35 U.S.C. § 120 of U.S. patent application Ser. No. 15/546,423, filed on Jul. 26, 2017, entitled "Internet-Linked Ultrasonic Network for Medical Devices," which is a national phase entry under 35 U.S.C. § 371 of International Application No. PCT/US2016/014860, filed on Jan. 26, 2016, which claims priority under 35 U.S.C. § 119(e) of U.S. Provisional Application No. 62/107,737, filed on Jan. 26, 2015, the disclosures of which are hereby incorporated by reference.

STATEMENT REGARDING FEDERALLY SPONSORED RESEARCH OR DEVELOPMENT

This invention was made with government support under Grant Number CNS-1253309 awarded by the National Science Foundation. The government has certain rights in the invention.

BACKGROUND

Wirelessly networked systems of implantable medical devices endowed with sensors and actuators may be the basis of many innovative therapies. Existing as well as futuristic applications of wireless technology to medical implantable and wearable devices are growing into a new market that several analysts are starting to refer to as "The Internet of Medical Things" (IoMT). Unfortunately, the dielectric nature of the human body poses a key obstacle to enabling this vision of networked implantable devices. Biological tissues are composed primarily (65%) of water, a medium through which radio-frequency (RF) electromagnetic waves, which are the physical basis of most commercial wireless technologies such as WiFi or Bluetooth, do not easily propagate. The human body absorbs, distorts, and delays RF signals. Since RF waves are absorbed by tissues, higher transmission power is needed to establish reliable communication links. This reduces the battery lifetime (or, equivalently, increases the battery size) of the implantable device, in a domain where low power, miniaturization, and battery duration are major concerns. A surgical procedure is, in most cases, needed to replace the batteries of implants. To put this in context, state-of-the-art pacemakers require power in the order of $\mu W$ for pacing, while a commercial RF transceiver for an implant operates with power in the order of tens of mW, making continuous telemetry operation prohibitive. As a consequence, in state-of-the-art pacemakers, the battery alone often occupies two thirds of the entire volume of the implant.

SUMMARY OF THE INVENTION

A hardware and software architecture of an Internet of Medical Things (IoMT) platform with ultrasonic connectivity for communications through body tissues is provided.

The IoMT platform incorporates a modular and reconfigurable hardware and software architecture that can be flexibly adapted to different application and system requirements to enable telemetry, remote control of medical implants, as well and implant-to-implant communications for closed-feedback loop applications.

Additionally, embodiments of size-, energy-, and resource-constrained devices are implemented based on the IoMT platform software and hardware architecture, i.e., an implantable IoMT-mote and a wearable IoMT-patch, that implement ultrasonic communication protocols and communicate with each other through ultrasounds. The IoMT-mote is a miniaturized software-defined implantable device with ultrasonic communication and networking capabilities. Embodiments of these devices are based on low-power miniaturized components, providing miniaturized wireless ultrasonic implantable devices. In some embodiments, their performance compares favorably with commercial RF-based wireless technologies, e.g., Bluetooth Low Energy (BLE).

A telemetry system is provided that is based on the two devices for real-time remote monitoring of biological parameters. The system can comprise multiple IoMT-motes with sensing capabilities deployed inside a human body that communicate through ultrasounds with an IoMT-patch attached to the body. The IoMT-patch can offer RF wireless connectivity to route the sensed information to a smartphone or to the cloud.

Other aspects of the method, device, and system include the following:

1. An ultrasound communication device for transmitting signals ultrasonically within a network of implanted and/or worn medical devices, comprising:

a communication unit comprising an ultrasonic transceiver to transmit and receive ultrasonic signals through biological tissue to and from other devices in the network of devices; and a processing unit in communication with the communication unit to receive signals from and transmit signals to the communication unit, the processing unit including a processor and memory, the processor operative to reconfigure in real time one or more upper layer protocols in a protocol stack and a reconfigurable logic device operative at a physical layer in the protocol stack.

2. The device of embodiment 1, wherein the processor is operative to reconfigure one or more of an application layer, a link layer, a media access control layer, and a network transport layer.

3. The device of any of embodiments 1-2, wherein the reconfigurable logic device is operative to control transmitter and receiver chains to transmit and receive ultrasonic transmissions.

4. The device of any of embodiments 1-3, wherein the reconfigurable logic device includes a register module operative to store and route configuration parameters determined by the processor, the configuration parameters including one or more of a spreading code, a spreading code length, a time-hopping frame length, a time-hopping sequence, a packet payload size, or a length of a preamble.

5. The device of embodiment 4, wherein the processor delivers to the register module the configuration parameters via a serial peripheral interface.

6. The device of any of embodiments 1-5, wherein the reconfigurable logic device includes a configurable serial peripheral interface (SPI) module.

7. The device of embodiment 6, wherein the SPI module is operative to configure communication settings, including one or more of data rate, clock polarity and clock phase.

8. The device of any of embodiments 6-7, wherein the SPI module is operative to enable communication with the processor or a peripheral device.

9. The device of any of embodiments 6-8, wherein the SPI module includes a master module in communication with the processor and a slave module.

10. The device of any of embodiments 6-9, wherein the SPI module is operative to trigger sampling operations on an analog to digital converter and to read back sampled digital waveforms.

11. The device of any of embodiments 1-10, wherein the reconfigurable logic device includes a field-programmable gate array, a masked-programmed gate array, an application specific integrated circuit, a small-scale integrated circuit, a programmable logic array, or a programmable logic device.

12. The device of any of embodiments 1-11, further comprising a sensing or actuating unit, and wherein the controller is operative in real time to trigger a reading from the sensing or actuating unit and to process the reading.

13. The device of embodiment 12, wherein the controller is further operative to transmit data processed from the reading to the logic device for transmission as an ultrasonic signal.

14. The device of any of embodiments 1-13, wherein the processing unit further includes an energy management module operative to adjust at runtime a core clock frequency according to processing power required, select at runtime a low-power mode, provide an automatic wake-up, or power up and shut down components.

15. The device of any of embodiments 1-14, wherein the communication unit further includes a receiver chain including an analog to digital converter operative to convert incoming ultrasonic analog signals to digital signals, and a transmitter chain including a digital to analog converter operative to convert outgoing digital signals to analog signals for ultrasonic transmission.

16. The device of any of embodiments 1-15, further comprising a sensor interface to enable connection between the processing unit and a sensor device or an actuating device.

17. The device of any of embodiments 1-16 in communication with a sensing device selected from the group consisting of a motion sensor, a gyroscope, an accelerometer, a cardiac rhythm monitor, a heart rate monitor, a pulse monitor, a blood pressure monitor, a glucose sensor, a drug pump monitor, a sleep sensor, a REM sleep duration sensor, a still camera, a video camera, a sensor for one or more biomolecules, a sensor for one or more pharmaceutical agents or pharmaceutical formulation ingredients, a sensor for a dissolved gas or ion, a sensor for pH, a sensor for ionic strength, and a sensor for osmolality.

18. The device of any of embodiments 1-17 in communication with an actuating device selected from the group consisting of a drug pump, a heart stimulator, a heart pacemaker, a bone growth stimulator, a deep brain stimulator, a neurostimulator, and a neuromuscular electrical stimulator.

19. The device of any of embodiments 1-18, wherein the device is implantable within a body or wearable on a skin surface of a body.

20. The device of any of embodiments 1-19, wherein the communication unit further includes a radio frequency (RF) interface operative to receive and transmit in-air RF transmissions, and wherein the device is wearable on a skin surface of a body.

21. The device of embodiment 20, wherein the device is in communication via said RF transmissions with a further device coupled to a communications network.

22. The device of any of embodiments 20-21, further comprising a wireless controller operative to connect to a Bluetooth Low Energy (BLE) access point device and/or to a 6LoWPAN device.

23. The device of embodiment 22, wherein the wireless controller includes a Message Queue Telemetry Transport (MQTT) client module that is operative to read data from the implantable device through the ultrasonic interface, and publish sensor readings to an MQTT broker.

24. The device of any of embodiments 22-23, wherein the wireless controller includes a Message Queue Telemetry Transport (MQTT) client module operative to open a connection with the MQTT broker through an IPv6 address, to authenticate an application, and/or publish new content.

25. The device of any of embodiments 1-24, wherein the processor is operative at a current of less than 7 mA during a run mode.

26. The device of any of embodiments 1-25, wherein the processor is operative at a current of less than 2 mA during a transmit state.

27. The device of any of embodiments 1-26, wherein the processor is operative at a current of less than 0.22 mA during a stop mode.

28. The device of any of embodiments 1-27, wherein the processor is operative at a current of less than 0.001 mA during a very low leakage mode.

29. The device of any of embodiments 1-28, wherein the processor is operative at a power level of less than 22 mW during a run mode.

30. The device of any of embodiments 1-29, wherein the processor is operative at a power level of less than 7 mW during a transmit state.

31. The device of any of embodiments 1-30, wherein the processor is operative at a power level of less than 0.6 mW during a stop mode.

32. The device of any of embodiments 1-31, wherein the processor is operative at a power level of less than 0.003 mW during a very low leakage mode.

33. The device of any of embodiments 1-32, wherein the logic device is operative at a current of less than 2 mA during a transmit state.

34. The device of any of embodiments 1-33, wherein the logic device is operative at a power level of less than 5 mW during a transmit state.

35. The device of any of embodiments 1-34, further comprising a casing of a biocompatible material, the communication unit and the processing unit housed with the casing.

36. The device of embodiment 35, wherein the casing is sized to be less than 2 cm in any one dimension.

37. The device of any of embodiments 35-36, wherein the casing is sized to be less than 1 cm in at least one dimension.

38. The device of any of embodiments 35-37, wherein the biocompatible material of the casing is titanium or a biocompatible polymer.

39. The device of any of embodiments 35-38, further comprising a skin patch for attaching the casing to a skin surface of a patient.

40. A system comprising:
   an RF/ultrasound communication device of embodiment 20; and
   one or more ultrasound communication devices of any of embodiments 1-39 implantable within a body and capable of ultrasound communication with the device of embodiment 20.

41. The system of embodiment 40, wherein the RF/ultrasound communication device is worn on a skin surface of a body and the one or more ultrasound communication devices are implanted within the body.

42. The system of any of embodiments 40-41, further comprising an access point device, including a communications interface operative to receive and transmit radio frequency transmissions with the RF/ultrasound communication device.

43. The system of any of embodiments 40-42, further comprising a one or more sensing devices selected from the group consisting of a motion sensor, a gyroscope, an accelerometer, a cardiac rhythm monitor, a heart rate monitor, a pulse monitor, a blood pressure monitor, a glucose sensor, a drug pump monitor, a sleep sensor, a REM sleep duration sensor, a still camera, a video camera, a sensor for one or more biomolecules, a sensor for one or more pharmaceutical agents or pharmaceutical formulation ingredients, a sensor for a dissolved gas or ion, and a sensor for pH, ionic strength or osmolality; wherein each sensing device is in communication with an ultrasound communication device of the system.

44. The system of any of embodiments 40-43, further comprising one or more actuating devices selected from the group consisting of a drug pump, a heart stimulator, a heart pacemaker, a bone growth stimulator, a deep brain stimulator, a neurostimulator, and a neuromuscular electrical stimulator; wherein each actuating device is in communication with an ultrasound communication device of the system.

45. A method of controlling a plurality of networked medical devices, the method comprising the steps of:

(a) providing the system of any of embodiments 40-44 further comprising one or more sensing devices and/or one or more actuating devices, each in communication with an ultrasound communication device of the system;

(b) configuring the protocol stack and logic device of each ultrasound communication device in the system;

(c) acquiring data from the one or more sensing devices and optionally processing the data;

(d) optionally communicating the data using the RF/ultrasound communication device, an access point, and the internet to a physician;

(e) optionally receiving reprogramming instructions using the RF/ultrasound communication device, access point, and internet;

(f) reconfiguring the protocol stack and logic device of one or more selected ultrasound communication devices in the system in response to the reprogramming instructions; and (g) optionally causing one or more of said actuating devices to change their actuation state.

46. The method of embodiment 45, wherein the reprogramming instructions include altering one or more of a data acquisition rate, a data transmission rate, and a type of data sensed by one or more of said sensing devices.

47. The method of any of embodiments 45-46, wherein the reprogramming instructions include one or more of altering a parameter, a duty cycle, and a state of one or more of said actuating devices.

48. The method of any of embodiments 45-47, wherein the reprogramming instructions include altering one or more of a dosage and a rate of administration of one or more agents.

49. The method of any of embodiments 45-48, wherein the reprogramming instructions include altering an instruction to one or more of said sensing devices or said actuating devices in response to a feedback algorithm.

50. The method of any of embodiments 45-49, wherein the reprogramming instructions include altering an instruction to one or more of said sensing devices or said actuating devices in response to a physiological or pathological state of a patient.

51. The method of any of embodiments 45-50, wherein the reprogramming instructions include triggering a reading from one or more of said sensing devices or said actuating devices and processing the reading.

52. The method of any of embodiments 45-52, wherein the reprogramming instructions include altering an instruction to adjust at runtime a core clock frequency according to a processing power requirement, select a low-power mode, provide an automatic wake-up, or power up or shut down instruction.

DESCRIPTION OF THE DRAWINGS

The invention will be more fully understood from the following detailed description taken in conjunction with the accompanying drawings in which.

DETAILED DESCRIPTION OF THE INVENTION

Figure 1:
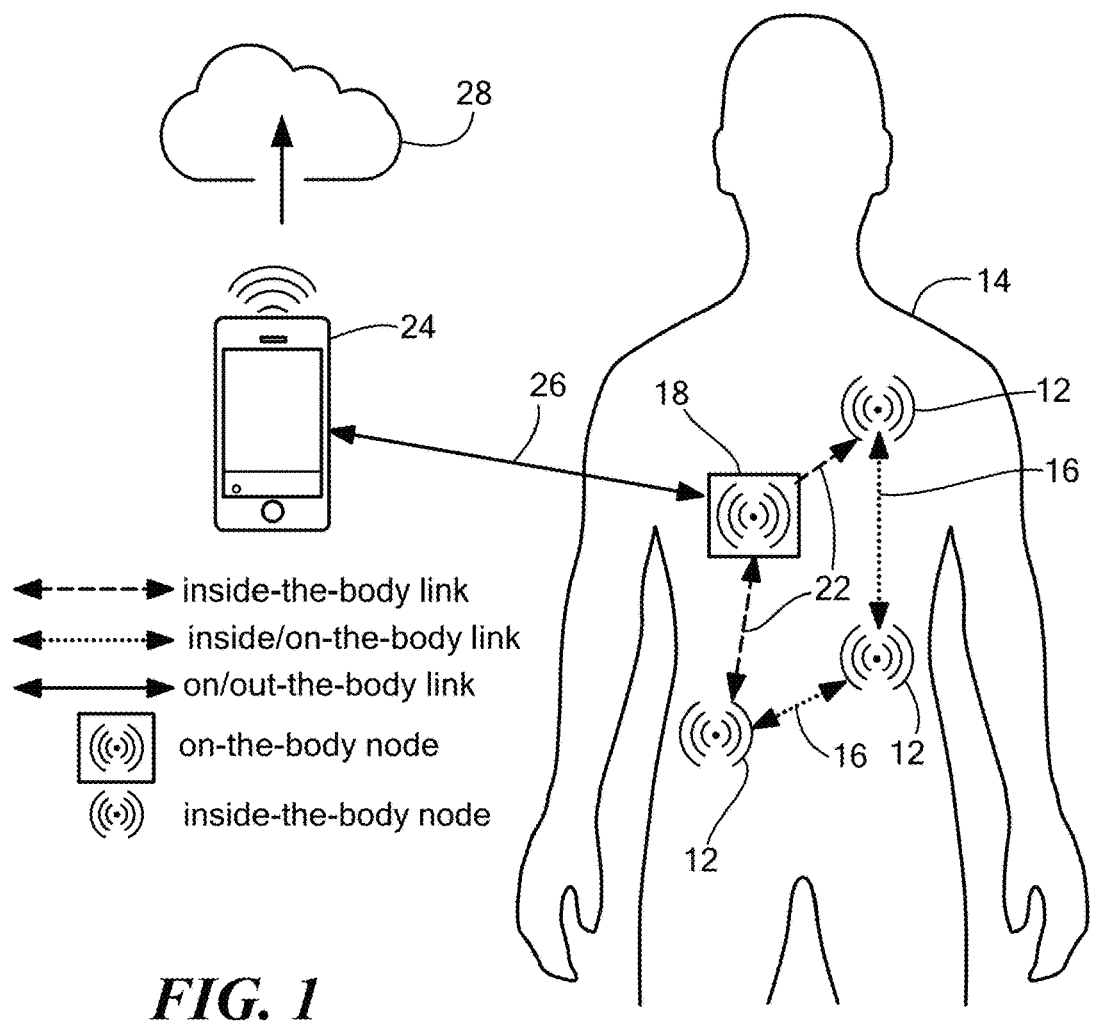
FIG. 1 is a schematic illustration of an embodiment of an Internet of Medical Things.

The present invention relates to embodiments of an Internet of Medical Things (IoMT) platform with ultrasonic wireless connectivity that can be used as a base for building future IoT-ready medical implantable and wearable devices that communicate safely, reliably and with low-power consumption through body tissues using ultrasounds instead of RF-waves. Ultrasounds are mechanical waves that propagate in elastic media at frequencies above the upper limit for human hearing, i.e., 20 kHz. Compared to RF-waves, ultrasounds have significantly lower absorption by human tissues (e.g., around 70 dB less attenuation for a 1 MHz ultrasonic link compared to a 2.45 GHz RF link over 10 to 20 cm); therefore, lower transmission power is needed, and implantable battery-powered devices can last longer and/or be smaller in size. Moreover, the medical experience of the last several decades has demonstrated that ultrasonic heat dissipation in tissues is minimal compared to RF, and for this reason, the FDA also allows much higher intensity for ultrasonic waves (720 mW/cm$^2$) in tissues as compared to RF (10 mW/cm$^2$). By using ultrasounds for connecting medical implants, patients can benefit from implants that provide wireless telemetry, reprogrammability and continuous real-time monitoring while minimally affecting the battery lifetime of the device. This reduces the number of surgical procedures required to replace the implant. Real-time remote monitoring applications can reduce in-office visits and hospitalization, leading to substantial savings in medical costs. Furthermore, low-power ultrasonic communications can enable advanced therapies that require wireless reliable communication through tissues between multiple implantable sensing and stimulating devices. From a security and reliability perspective, the ultrasonic communications cannot be easily eavesdropped or jammed without physical contact. Additionally, ultrasounds eliminate electromagnetic compatibility concerns of a crowded RF spectrum. It is therefore safer and transparent to the RF spectrum management procedures of healthcare facilities.

The system includes a set of software-defined cross-layer functionalities tailored for networking ultrasonic wearable devices that offer real-time reconfigurability at different layers of the protocol stack, i.e., the physical (PHY), data link, network and application layer. More specifically, the system encloses a set of PHY, data link and network functionalities that can flexibly adapt to the application and system requirements, to optimally network information between ultrasonic wearable devices. The system also offers real-time reconfiguration at the application layer to provide a flexible platform to develop medical applications. In particular, the system includes sensor data processing applications running in nodes of a network that can be decomposed into primitive building blocks that can be arbitrarily arranged to create new sensing applications to fit the user requirements.

Embodiments of the system and method can employ aspects at different layers of the protocol stack to overcome limitations posed by the propagation characteristics of ultrasonic waves in air. For example, two signaling schemes, GMSK and orthogonal frequency-division multiplexing (OFDM), can be suitably used because of their high spectral efficiency and resilience to multipath. Two different synchronization modes can be alternatively and suitably used for channels strongly affected by multipath or by Doppler effect. Upper layer protocols and functionalities can be selected to address challenges posed by the long propagation delays of ultrasounds in air that might prevent accurate timing.

Ultrasounds are mechanical pressure waves that propagate through elastic media at frequencies above the upper limit for human hearing, i.e., 20 kHz.

Attenuation.

Two main mechanisms contribute to ultrasound attenuation in tissues, i.e., absorption and scattering. An initial pressure $P_0$ decays at a distance d $$P(d)=P_0 e^{-\alpha d}$$

where $\alpha$ (in [Np·cm$^{-1}$]) is an amplitude attenuation coefficient that captures all the effects that cause dissipation of energy from the ultrasound wave. Parameter $\alpha$ depends on the carrier frequency through $\alpha = af^b$, where f represents the carrier frequency (in MHz) and a (in [Np m$^{-1}$ MHz$^{-b}$]) and b are attenuation parameters characterizing the tissue.

Two mechanisms mainly contribute to acoustic attenuation in air, i.e., spreading loss and absorption loss. The former includes spherical spreading, i.e., the acoustic pressure falls off proportionally to the surface area of a sphere. The latter is mainly related to atmospheric absorption caused by the interaction of the acoustic wave with the gas molecules of the atmosphere and is frequency, temperature, and humidity dependent.

For a signal at frequency f [Hz] over a transmission distance d [m], the attenuation can be expressed in [dB] as $$A_{dB}=20 \log_{10}(d)+d\alpha(f),$$

where $\alpha(f)$ [dB/m] is the absorption coefficient, which increases quadratically with the frequency, but also depends on the ambient atmospheric pressure, temperature, and the molar concentration or water vapor, i.e., humidity.

Propagation Speed.

Ultrasonic wave propagation is affected by propagation delays that are orders of magnitude higher than RF. The propagation speed of acoustic waves in biological tissues is approximately 1500 m/s, as compared to 2×10$^8$ m/s for RF waves.

The propagation speed of acoustic waves in air is approximately 343 m/s at a temperature of 20° C. and at atmospheric pressure of 101.325 kPa, as compared to 3×10$^8$ m/s for RF electromagnetic waves. The speed of sound in air increases with temperature and humidity, going from 331 m/s at a temperature of 0° C. and 10% relative humidity to 351 m/s at a temperature of 30° C. and 90% relative humidity.

Operating Frequency.

Considerations in determining the operating frequency are (i) the frequency dependence of the attenuation coefficient, and (ii) the frequency dependence of the beam spread of ultrasonic transducers (which is inversely proportional to the ratio of the diameter of the radiating surface and the wavelength). Therefore, higher frequencies help keep the transducer size small, but result in higher signal attenuation. Since most biomedical sensing applications require directional transducers, one needs to operate at the lowest possible frequencies compatible with small-size transducers and required signal bandwidth. For propagation distances in the order of several cm. the operating frequency should not exceed 10 MHz.

Doppler Spreading.

Doppler spreading occurs as a result of Doppler shifts caused by relative motion between source and receiver, and is proportional to their relative velocity. Doppler spreading generates two different effects on signals: a simple frequency translation, and a continuous spreading of frequencies that generates intersymbol interference (ISI), thus causing degradation in the communication performance. Since the speed of sound is several orders of magnitude lower than the speed of electromagnetic waves, the resulting Doppler effect is severe, even at relatively low speeds.

Reflections and Scattering.

The human body is composed of different organs and tissues with different sizes, densities and sound speeds. Therefore, it can be modeled as an environment with pervasive presence of reflectors and scatterers. The direction and magnitude of the reflected wave depend on the orientation of the boundary surface and on the acoustic impedance of the tissues, while scattered reflections occur when an acoustic wave encounters an object that is relatively small with respect to its wavelength or a tissue with an irregular surface. Consequently, the received signal is obtained as the sum of numerous attenuated, possibly distorted, and delayed versions of the transmitted signal.

The on-body ultrasonic channel is composed of several interfaces between air and human body, and between air and on-body and near-body objects. Because of this inhomogeneous pattern, the on-body channel can be modeled as an environment with pervasive presence of reflectors and scatterers. The direction and magnitude of the reflected wave depend on the orientation of the boundary surface and on the acoustic impedance of the different media involved. Scattered reflections occur when an acoustic wave encounters an object that is relatively small with respect to its wavelength. (The acoustic impedance is defined as the product between the density of a medium p and the speed of sound in the medium c.) Consequently, the received signal is obtained as the sum of numerous attenuated, possibly distorted, and delayed versions of the transmitted signal.

Ultrasonic Transducers.

An ultrasonic transducer is a device that converts electrical signals into ultrasonic signals and vice versa. Ultrasonic transducers can be categorized into two main classes based on the physical mechanism that enables the conversion, i.e., piezoelectric and electrostatic transducers. A piezoelectric transducer produces a mechanical vibration through a thin piezoelectric element under an external voltage variation, and produces a voltage variation under an external mechanical vibration. In electrostatic transducers the fundamental mechanism is the vibration of a thin plate under electrostatic forces.

When sound passes across an interface between two materials, it is in part transmitted and in part reflected. To maximize the acoustic energy radiated by the transducer, the acoustic impedance of the radiating surface should match the acoustic impedance of the propagation medium. Today, microelectro-mechanical (MEMS) technology has enabled the fabrication of microscopic piezoelectric and electrostatic transducers, i.e., so-called Micromachined Ultrasonic Transducers (MUTs). With MUTs, the acoustic impedance can be controlled to match the external medium by manipulating the device geometry. This characteristic makes MUTs suitable for air-coupled applications.

When the operating frequency of the ultrasonic communications falls in the near-ultrasonic frequency range, i.e., 15 to 17 kHz to 20 to 22 kHz, acoustic waves can be recorded and generated using components, such as microphones and speakers, which can be commercial off the shelf (COTS) components. Even though COTS components are often designed to operate a lower frequencies, i.e., at 0-17 kHz, they can still sense and generate, albeit less efficiently, near-ultrasonic frequency waves. Since many commercial devices such as smartphones, tablets and laptops among others, are equipped with audio interfaces, they can in some embodiments, support near-ultrasonic communications with no additional hardware.

I. IOMT PLATFORM ARCHITECTURE

Embodiments of an IoMT platform provide a modular software and hardware architecture to be used as a basis for future low-power IoMT-ready wearable and implantable devices that communicate wirelessly through ultrasounds. Embodiments of the IoMT platform allow the ability to (i) remotely measure, store, and manage on the cloud vital physiological parameters of a patient measured by the implantable sensors (telemetry); (ii) remotely control actuators deployed in the body of the patient, e.g., stimulators, controlled drug pumps, and pacing devices; (iii) enable closed-loop feedback applications. For example, a smart coronary stent could detect potential clogs and allow the doctor to remotely monitor the patient condition and automatically trigger injection of drugs that prevent artery re-occlusion. Furthermore, the ultrasonic IoMT platform can also support implant-to-implant communication through entirely intra-body communication links. This can enable closed-loop applications where actuators perform an action (e.g., stimulate) based on physiological data captured by sensors implanted elsewhere in the body. For example, a smart neurostimulator can be triggered by a motion sensor or a heart rate sensor to anticipate an epileptic attack.

FIG. 1 shows an embodiment of a general application scenario enabled by the IoMT platform, where a set of sensors and actuators, here IoMT-motes 12, deployed inside the body 14 of a patient that communicate with each other through inside-the-body ultrasonic links 16 (dotted lines), and also with wearable devices, here IoMT-patches 18, deployed along or on the body of the patient (dashed lines) 22. The IoMT-patches can enable communication from the intra-body network to an access point device 24, e.g., a smartphone or a gateway, through traditional radio frequency-based technologies 26, e.g., BLE or 802.15.4/6LOWPAN. The access point device connects the system to the user and to the Internet 28 enabling remote monitoring, control and cloud storage on a server.

A. Hardware Architecture

Figure 2:
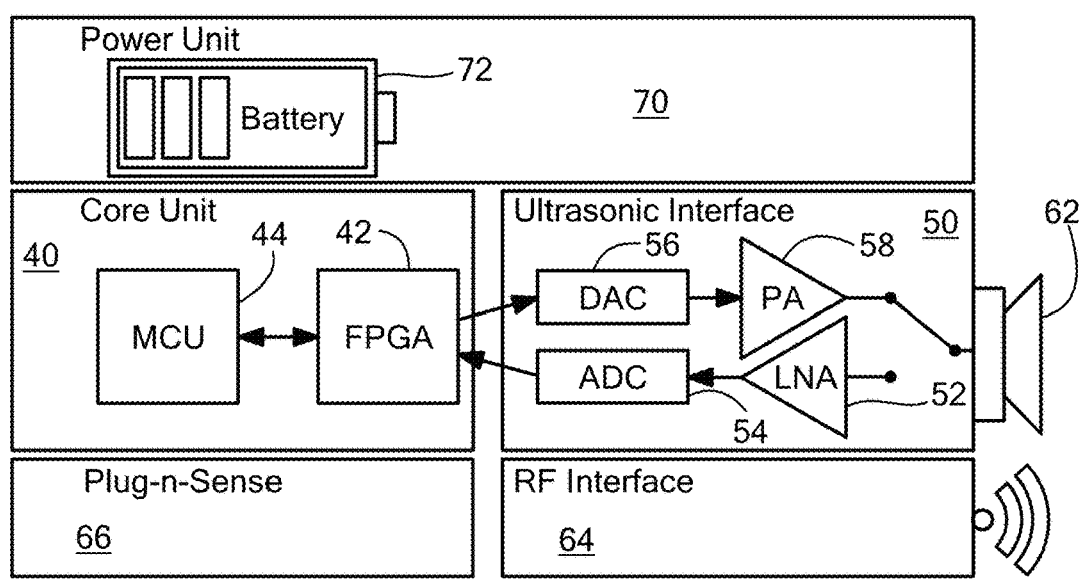
FIG. 2 is a schematic illustration of an Internet of Medical Things platform hardware architecture.

The IoMT-mote and the IoMT-patch (IoMT-devices in general) are based on embodiments of an ultrasonic IoMT platform modular hardware architecture, shown in FIG. 2. The core unit 40 of the node includes (i) reconfigurable logic device 42, such as a mm-size low-power field programmable gate array (FPGA), (to enable flexible hardware reconfiguration in charge of executing physical layer protocols) and (ii) a micro controller unit (MCU) 44. Their combination offers hardware and software reconfigurability with very small packaging and low energy consumption. The miniaturized FPGA hosts the physical (PHY) layer communication functionality. Reconfigurability at the physical layer is desirable—implants have often a lifetime of 5 to 10 years at least, while wireless standard chipsets have a lifetime of 1.5 years and become soon outdated. The MCU is in charge of data processing and of executing software-defined functionality to implement flexible and reconfigurable upper-layer protocols, e.g., non-time critical MAC functionality, network, transport and application. The ultrasonic interface 50 enables ultrasonic wireless connectivity for both the IoMT-motes and the IoMT-patches, and includes a receiver (Rx) and a transmitter (Tx) chain. The Rx chain includes a low-noise amplifier 52 and an analog-to-digital converter (ADC) 54 to amplify and digital-convert received signals, while the Tx chain embeds a digital-to-analog converter (DAC) 56 and a power amplifier (PA) 58 to analog-convert and amplify the digital waveform before transmission. Tx and Rx chains are in charge of transmitting and receiving digital streams through the ultrasonic transducers 62. The hardware architecture also embeds an RF interface 64 with an antenna to enable in-air RF wireless connectivity for example to connect the IoMT-patches to an access point. The Plug-n-Sense (PnS) Unit 66 includes a set of standard interfaces that allow the IoMT-mote to connect with different sensors, e.g., pressure and glucose sensors, to the ultrasonic IoMT platform according to the application and therapy requirements. Also in some embodiments, the IoMT-patch can implement sensing capabilities for measuring vital biomedical parameters available on the body surface, e.g., ECG signal or motion data. The PnS Unit can offer both standard digital and analog interfaces to accommodate different classes of sensors. The power unit 70 accommodates a battery 72 and voltage regulation system for powering the device.

Figure 3A:
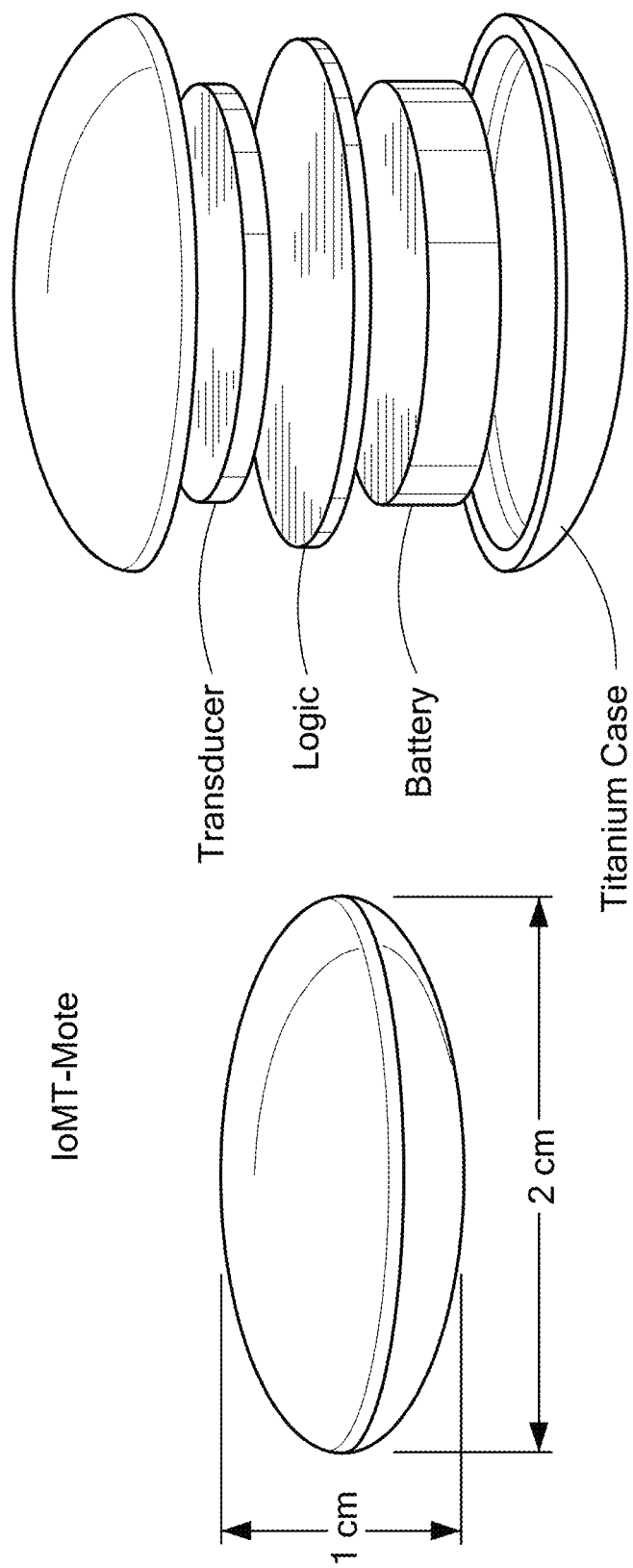
FIG. 3A is a schematic illustration of an embodiment of an IoMT-mote.
Figure 3B:
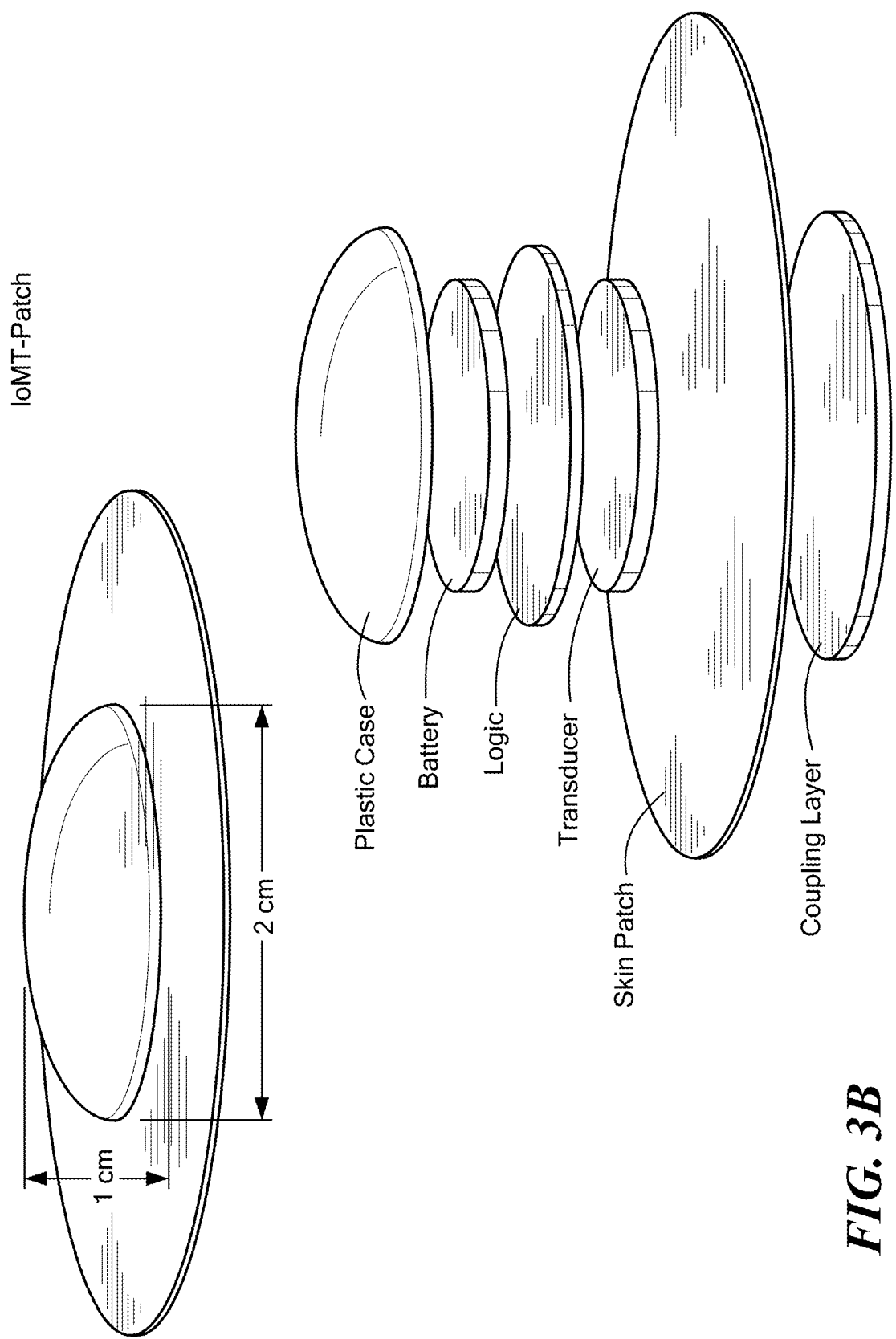
FIG. 3B is a schematic illustration of an embodiment of an IoMT-patch.

FIG. 3 shows embodiments of the IoMT-mote and the IoMT-patch including the logic, the battery, the ultrasonic transducer, and the casing. The IoMT-devices can be miniaturized. In some embodiments, the dimensions can be 1 cm×2 cm. In some embodiments, the IoMT-mote can be enclosed in a titanium biocompatible casing, The IoMT-patch can be enclosed in a plastic casing and attached to a disposable adhesive patch.

B. Software Architecture

Figure 4:
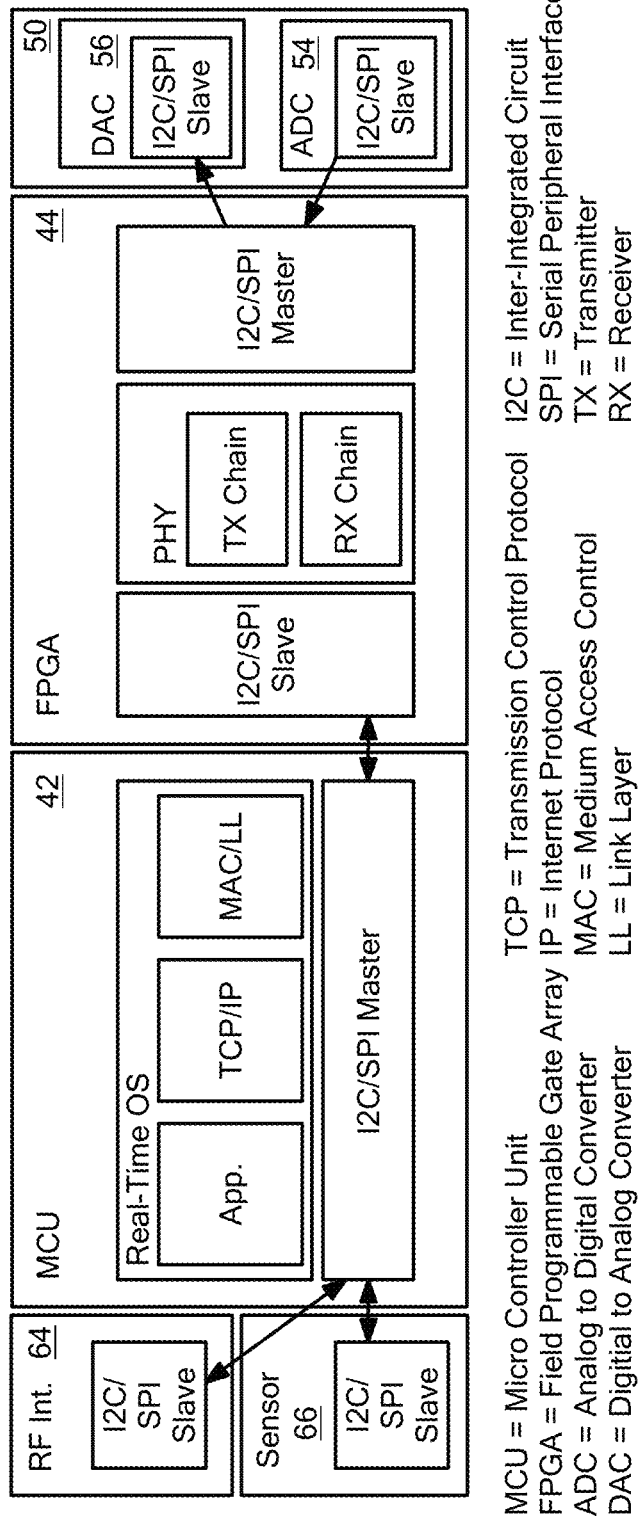
FIG. 4 is a schematic illustration of an IoMT platform software architecture.

In some embodiments, the IoMT platform can include a software-defined architecture designed to network IoMT-devices that encloses a set of PHY, data link and network layer functionalities that can flexibly adapt to the application and system requirements to efficiently distribute information. The IoMT software framework can provide real-time reconfigurability at the application layer to provide a flexible platform to develop medical applications. In some embodiments, sensor data processing applications running in the nodes are decomposed into primitive building blocks that can be arbitrarily arranged to create new sensing applications that fit the application requirements. FIG. 4 illustrates an embodiment of a high level description of an IoMT software architecture. The FPGA 44 logic design implements the PHY layer communication functionalities, as well as the interfaces, e.g., SPI and I2C, to connect the FPGA chip with the MCU 44 and the peripherals (DAC 56, ADC 54). The MCU software design can be based on a real-time operating system (RTOS) and executes the upper layer communication functionality and protocol, e.g., link layer (LL), Medium Access control (MAC), Network and Application layer. In some embodiments, the MCU software design defines SPI and I2C interfaces to enable data exchange between the MCU and the peripherals (FPGA 44, RF interface 46 and sensors 66).

II. IOMT-MOTE DEVICE

Described herein are embodiments of a IoMT-mote device, which may also be termed an implantable device or node, that can be based on the IoMT platform software and hardware architecture discussed above in Section I.

A. Hardware Implementation

Figure 5:
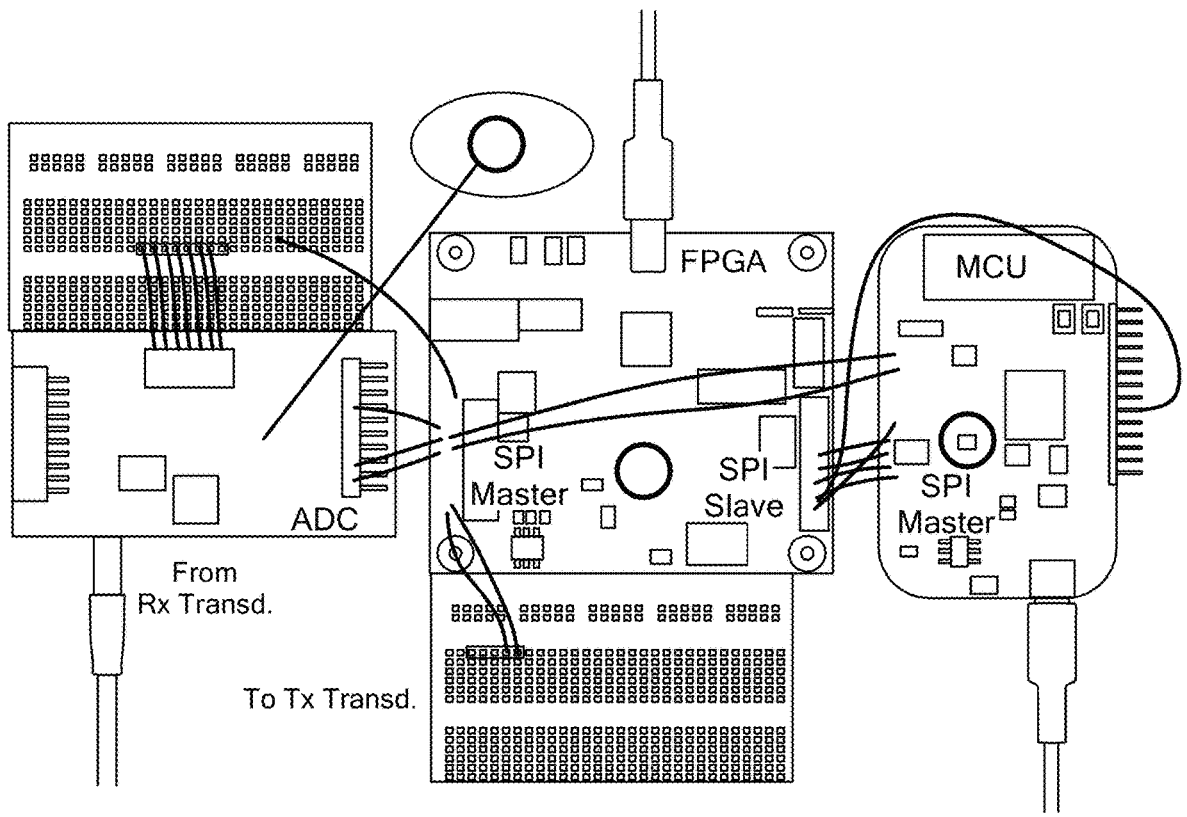
FIG. 5 is an illustration of an ultrasonic alpha-prototype node not including a preamplifier.

FIG. 5 shows an embodiment of a hardware implementation in a prototype stage, i.e., using development boards for each component connected through wires. Circles highlight the main integrated circuit in each development board. The ADC evaluation board is flipped for wiring convenience, therefore the front side with ADC is shown in a bubble above. The ADC receives data directly from the Rx ultrasonic transducer. The FPGA outputs digital waveforms to the Tx ultrasonic transducers. The FPGA is connected to the MCU and ADC evaluation board through SPI interfaces as slave and master, respectively. (See FIG. 4.) In this setup, the receiver preamplifier board, as well as the RF Interface board are not included. In some embodiments, all the components can be integrated into a printed circuit board enclosed in a biocompatible case as shown in FIG. 3A.

1) Core Unit: The core unit of the node includes (i) a mm-size low-power field programmable gate array (FPGA) and (ii) a micro controller unit (MCU).

FPGA.

In one embodiment, a Lattice Semiconductor iCE40 Ultra is used, which is a commercially available small, low power, and integrated FPGA. It offers 4 k look-up-tables (LUTs) in a very small 36-ball wafer level chip scale package (2.08× 2.08 mm) with very low static current drain (71 µA). The FPGA operates with 1.2 V and 3.3 V dual voltage for the core and the digital input/output, respectively. The breakout evaluation board that Lattice offers for the iCE40 Ultra is used, which provides the FPGA with a clock of 12 MHz.

MCU.

The MCU is in charge of executing functionalities to coordinate the transmission operation and implement upper-layer protocols. Mm-size packaging and low-power consumption are desirable requirements in this embodiment. Therefore a Freescale Kinetis KL03 ultra-low-power MCU is used. The KL03 MCU is a 32-bit ARM Cortex-M0+ core in an ultra-small chip-scale package 1.6×2.0 mm specifically designed to develop smart and miniaturized devices. The tiny packaging and low-energy functionalities make Freescale Kinetis KL03 a suitable match for this embodiment. The KL03 also embeds a 12-bit ADC with up to 818 kHz sampling frequency that can be used to interface the MCU with external analog sensing devices. For this embodiment, a FRDM-KL03Z, a breakout evaluation board for the KL03 MCU is used.

2) Ultrasonic Interface: The ultrasonic interface enables ultrasonic wireless connectivity through data converters, low-noise amplifiers (LNA), and custom ultrasonic transducers.

Ultrasonic Transducers.

The IoMT-mote embodiment embeds a miniaturized ultrasonic transducer to generate and receive ultrasonic waves. The transducer operates around 700 kHz, and is based on a thin-disk piezoelectric element that offers relative large bandwidth, i.e., around 200 kHz, with no need for any backing material that would increase the transducer size.

Figure 6:
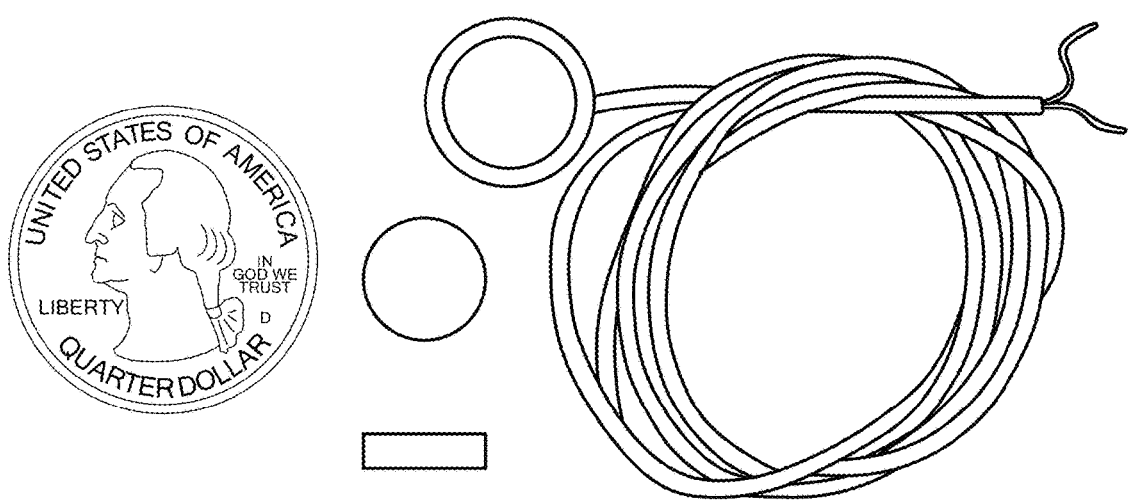
FIG. 6 is an illustration of ultrasonic transducers with and without casing.

The piezoelectric element is around 9.5 mm in diameter, and has a thickness of about 3 mm. 700 kHz can be selected as an operating frequency because it offers a good tradeoff between attenuation of ultrasounds in tissue (increasing with frequency), thickness of the piezoelectric element (increasing with frequency), available bandwidth (increasing with frequency), and radiation directivity (increasing with frequency). A diameter of 9.5 mm is selected because it is a good tradeoff point between size, conversion loss (increasing with smaller disks), and directionality (decreasing with smaller disks). In some embodiments, there can be 6 dB of conversion loss of the transducers between transmitting and the receiving transducers, when ideally no attenuation is introduced by the medium, e.g., short distance in water. Assuming the electric-to-acoustic and acoustic-to-electric efficiency to be equal, the conversion efficiency can be obtained as half the measured loss. In the embodiments described, the disk is embedded in an epoxy waterproof casing, which includes coupling layer, electrodes, and a micro-coaxial cable. In some embodiments, the IoMT-mote can embed the raw piezoelectric disk together with the logic and the battery in a casing. FIG. 6 shows an embodiment of the ultrasonic transducer with casing, as well as the piezoelectric element compared with a quarter for size.

ADC.

In some embodiments, the device can operate at 700 kHz central frequency, with a −3 dB bandwidth of about 200 kHz. In some embodiments, a sampling frequency of the ADC can be fixed around 2 MHz. In some embodiments, a small low-power data converter, e.g., a TI ADS7883 commercially available from Texas Instrument (TI), can be used, which satisfies the sampling rate parameters. The ADC, e.g., the ADS7883, can be connected to the FPGA through an SPI interface as slave peripheral and clocked by the FPGA that operates as SPI master. In some embodiments, the SPI connection uses three pins to output data through SPI protocol, i.e., clock, enable, and data out. This reduces the converter sizes compared to parallel converters, where samples are loaded in parallel requiring as many pins as the number of bits per sample. Having fewer pins is useful when a limited number of pins is available on the FPGA, e.g., 36 in total. In some embodiments, the ADC, e.g., the ADS7883, can offer a power-down mode where current consumption is as low as 1 1 µA, and TI offers breakout evaluation boards that include fully functional circuit designs with voltage reference and amplification circuits, as well as I/O accessible via headers.

Since the ADC operates serially on 16-bit samples (12 information bits and 4 control/padding bits), for a sampling rate of 2 MHz, the SPI link operates at 32 Mbit/s, which is achieved by feeding the SPI Master with a 32 MHz clock.

Driving the entire FPGA logic with an external 32 MHz clock rate is certainly possible, but can be undesirable because it would lead to unnecessary high dynamic power consumption, which is proportional to the circuit clock frequency and results from signal switching activity. Accordingly, an ultra-low power PLL, which is included in the iCE40 Ultra FPGA (described further below), can be used, to internally synthesize the 32 MHz clock from the 12 MHz clock on the FPGA evaluation board to individually drive the SPI Master block. By using the PLL to synthesize the high frequency clock signal, the rest of the logic can be driven with the original lower-frequency external clock signal, e.g., 12 MHz. Also, the PLL can be turned into low-power mode to minimize the energy consumption when communication with the ADC and DAC is not needed.

LNA.

In some embodiments, the ADC, e.g., the ADS7883 ADC, can accept a unipolar input ranging in 0 to $V_{cc}$. A signal conditioning circuit can be used to offset the input signal at the receiver from DC to $V_{cc}/2$. The signal conditioning circuit can be implemented using a low-noise, low-distortion and low power operational amplifier (e.g., TI OPA835) configured as an inverting gain of 1 that shifts the signal to the desired DC offset of $V_{cc}/2$ and consumes as low as 250 µA when powered on.

In some embodiments, to increase the receiver sensitivity and therefore being able to operate at lower transmission powers, a low noise and variable gain amplifier (VGA) can be used before the signal conditioning circuit. For example, the AD8338 VGA offers low current consumption, i.e., 3 mA, and a voltage controlled gain between 0 to 80 dB. By reducing the transmission power, energy can be saved at the transmitter, but the power consumption is increased at the receiver to power the preamplifier. Therefore, the use of the VGA can be application dependent.

Tx Chain.

In some embodiments, in the Tx chain, a low-power, low-complexity and low-cost solution can be implemented that does not require a DAC to convert digital waveforms to analog. Because of the impulsive nature of the UsWB transmission scheme, in some embodiments, the system can transmit digital square pulses (0 to $V_{cc}$) from the digital output of the FPGA, with no need for analog conversion. The digital pulses can be directly fed into the transducer that filters out the out-of-band frequency components, and therefore shapes the square wave into a sine wave centered in 700 kHz. By avoiding the DAC, the size and energy consumption can be reduced, as well as the complexity and cost of the device. In this implementation, a power amplifier is not used, since the output power of the FPGA output pin is sufficient to satisfy the communication link budget requirements.

3) Power Unit: In some embodiments, the power unit can be a commercial power supply that offers adjustable voltage level, as well as onboard voltage regulators that allow each board to be powered through USB. In some embodiments, the power unit can accommodate a small implantable-grade battery with, e.g., 3.3 V nominal voltage. A low-dropout (LDO) regulator (e.g., TI TLV716P) can be used to generate the 3.3 V required to power the MCU. The other components can be powered through the MCU pins that can output up to 25 mA, and allows powering flexibility to reduce the energy consumption of the system, as discussed in Section II-B2 below. In some embodiments, the power unit can embed two integrated circuits that manage the human energy harvesting and ultrasonic energy transferring functionalities. The former allows the harvesting of vibrational energy available in the body, e.g., heart beat or human voice reverberations. The latter allows the collection of energy from ultrasonic waves transferred from an out-the-body ultrasonic source.

4) Sensing and/or Actuating Unit Interface: In some embodiments, the implantable node can include a flexible interface system to accommodate different sensing or actuating units, e.g., pressure and glucose level sensors, and actuating units, e.g., leads for electrical stimulations or micro-needles. The implantable node board can employ small pin headers where different detachable and interchangeable boards, i.e., daughter boards, can be connected. Each daughter board can accommodate different sensing or actuating units, making the implantable node a flexible sensing and actuating medical platform operable with many applications. The communication between the implantable node main board and the daughter boards can be handled by the MCU or the FPGA through serial or parallel connections. It will also be appreciated that a sensing and/or actuating unit can be hard wired to the implantable node.

Sensing units can include, for example and without limitation, a motion sensor, a gyroscope, an accelerometer, a cardiac rhythm monitor, a heart rate monitor, a pulse monitor, a blood pressure sensor, a glucose sensor, a drug pump monitor, a sleep sensor, a REM sleep duration sensor, a still camera, a video camera, a sensor for one or more biomolecules, a sensor for one or more pharmaceutical agents or pharmaceutical formulation ingredients, a sensor for a dissolved gas or ion, and a sensor for pH, ionic strength or osmolality. The sensor for one or more biomolecules can be a sensor for one or more peptides, oligopeptides, polypeptides, proteins, glycoproteins, antibodies, antigens, nucleic acids, nucleotides, oligonucleotides, polynucleotides, sugars, disaccharides, trisaccharides, oligosaccharides, polysaccharides, lipids, glycolipids, proteolipids, cytokines, hormones, neurotransmitters, metabolites, glycosaminoglycans, and proteoglycans.

Actuating units can include, for example and without limitation, a drug pump (such as an insulin pump), a heart stimulator (such as a defibrillator), a heart pacemaker, a bone growth stimulator, a deep brain stimulator, a neurostimulator, an electrode or electrode array, and a neuromuscular electrical stimulator.

B. Software Implementation

As discussed in Section I-B above, the FPGA logic can be mainly in charge of implementing the PHY layer functionality, while the MCU runs the MAC and LL functionality, IPv6 integration, as well as application layer functionality, such as sensor data acquisition and reconfigurable data processing operations. In some embodiments, a software-defined implementation can be used for the UsWB transmission scheme and protocol. UsWB is an impulse-based ultrasonic transmission and multiple access technique based on the idea of transmitting short information-bearing carrierless ultrasonic pulses, following a pseudo-random adaptive time-hopping pattern with a superimposed spreading code of adaptive length. Impulsive transmission and spread-spectrum encoding combat the effects of multipath and scattering and introduce waveform diversity among interfering transmissions.

Figure 22:
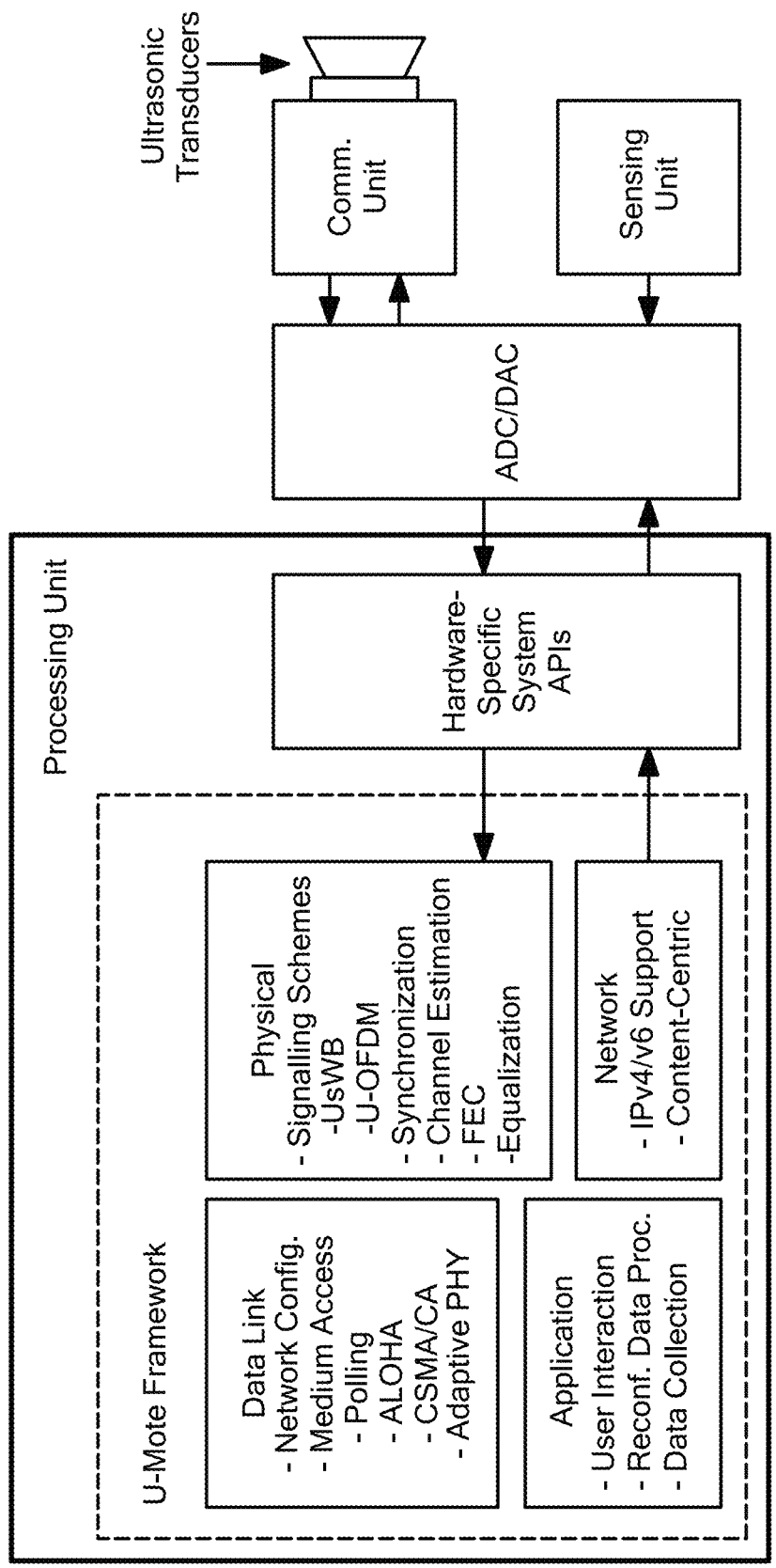
FIG. 22 is a schematic illustration of an overview of an implantable node networking framework.

The implantable node software architecture can include a software-defined networking framework that encloses a set of PHY, data link and network layer functionalities that can flexibly adapt to the application and system requirements to efficiently distribute information. The implantable node framework can also offer real-time reconfigurability at the application layer to provide a flexible platform to develop medical applications. In particular, sensor data processing applications running in the nodes can be decomposed into primitive building blocks that can be arbitrarily arranged to create new sensing applications that fit user requirements. FIG. 22 shows a high-level overview of an embodiment of the framework. It can include (i) PHY layer functionalities, including modulation and synchronization, for impulsive transmissions, (ii) data link layer functionalities including forward error control and medium access control (MAC) protocols, (iii) network layer functionalities, e.g., IPv4 and IPv6 support and content-centric networking, and (iv) application layer functionalities, i.e., reconfigurable sensing data processing and user interface. In some embodiments, these functionalities can be split into two different processing units. The data link, networking and application layer functionalities can be run on the MCU, and computationally demanding operations can be offloaded to the FPGA.

The implantable node networking framework provides interoperability with the Internet by defining an adaptation layer that integrates IPv4 and IPv6 protocol support. The adaptation layer includes a set of functionalities that interface the traditional IP network layer with the implantable node MAC layer through IP header compression and IP packet fragmentation functions optimized for ultrasonic networks. Standard protocols, such as TCP or UDP, or custom protocols can be implemented at a transport layer.

In some embodiments, the implantable node software architecture can be split between the FPGA and MCU. The FPGA logic design can implement the PHY layer communication functionalities, as well as the interfaces, e.g., SPI and I2C, to connect the FPGA chip with the MCU and the peripherals (DAC, ADC, memory and sensors). The MCU software design can be based on a real-time operative system (RTOS) and can execute the upper layer communication functionalities and protocol. The MCU software design can also define interfaces, e.g., SPI and I2C, to enable data exchange between the MCU and the peripherals (FPGA, DAC, ADC, memory and sensors).

In some embodiments, the MCU software architecture can implement the upper layer networking functionalities and protocols. The software design can be based on a real-time operating system (RTOS) that provides real-time performance and at the same time can offer a small and configurable footprint. Specifically, the RTOS can in a resource constrained environment. The RTOS can offer low-power functionalities, and can support SPI and I2C drivers to enable communications with the external peripherals (FPGA, DAC, ADC, memory and sensors). The RTOS can integrate the TCP/IP stack to enable the implantable node to support internet-of-things (IoT) applications. The RTOS can run application layer processing related to sensing or actuating operations. A number of commercial or open source RTOSs can be used, such as FreeRTOS or μTasker.

1) FPGA Design: In some embodiments, the FPGA top-level module can instantiate Tx and Rx chain blocks implementing the UsWB transmitter and receiver, respectively, as well as the SPI, PLL and register manager modules. In some embodiments, the FPGA top-level module can instantiate Tx and Rx chain blocks that implement the PHY layer communication functionalities, a set of first-in-first-out (FIFO) memory queue blocks, and a phase-locked loop (PLL) block. The logic can be driven by an external system clock signal input to one of the FPGA's pin.

Figure 7:
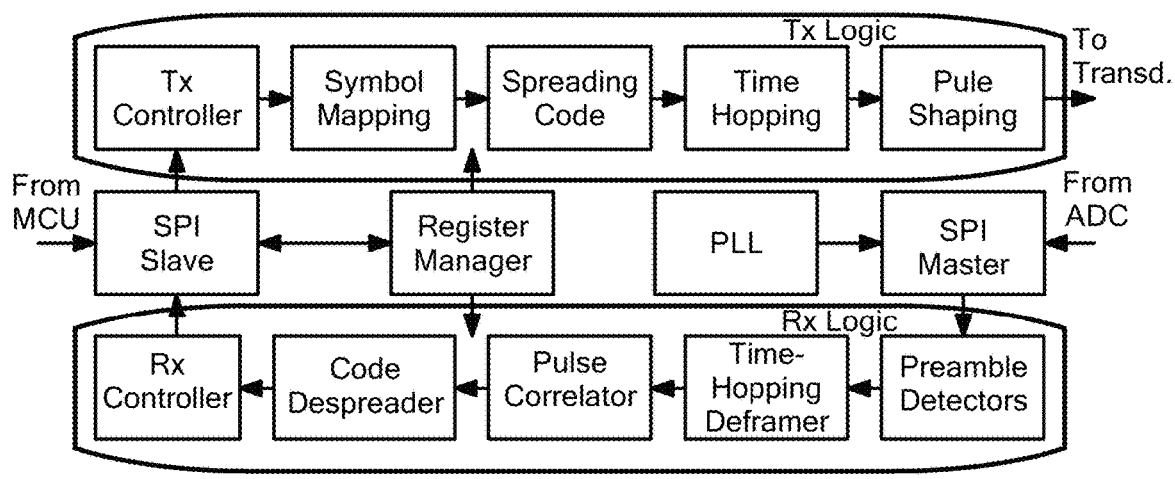
FIG. 7 is a schematic block diagram of an embodiment of an FPGA design including Tx and Rx chains with SPI, PPL and Register Manager modules.

UsWB PHY layer assumes time divided in slots of duration $T_c$, with slots organized in frames of duration $T_f = NT_c$, where N is the number of slots per frame. Each user transmits one pulse per frame in a slot determined by a pseudo-random time-hopping sequence. Bits mapped into pulses through pulse position modulation (PPM), i.e., a '0' bit is carried by a pulse delayed by a time δ with respect to the beginning of the slot, while a '1' symbol begins with the slot. Since a single pulse may collide with pulses transmitted by other users with a probability that depends on the frame size N, UsWB also adopts a spreading codes scheme where each information bit is mapped with a pseudo-orthogonal code of variable length, M. FIG. 7 shows a block diagram of an embodiment of the FPGA design implemented on the iCE40 Ultra.

Tx/Rx Chain.

The Tx and Rx chain blocks implement the transmitter and receiver PHY layer functionalities, respectively. This block gets as input a stream of bytes coming from the MCU though SPI, and outputs the PHY digital waveforms representing the modulated bits. The digital waveforms are then passed to the DAC through SPI, digital-to-analog converted, amplified by the PA, and then transmitted from the ultrasonic transducers.

On the receiver side, the signal captured by the receiver ultrasonic transducers is first amplified by the LNA and then analog-to-digital converted by the ADC. The digital waveforms are input through SPI to the Rx chain. This block can perform on the input waveforms digital signal processing operations such synchronization, channel estimation, and demodulation. The output of this block is a stream of bytes that can then be passed to the MCU via SPI.

Both the Tx chain and the Rx chain can run computationally complex operations, e.g., correlations, fast-Fourier transforms (FFTs), or digital filtering, among others, which are needed to implement PHY layer functionalities.

Tx Chain Design.

In some embodiments, the Tx chain can receive as input a stream of bytes coming from the MCU through the SPI Slave module, and outputs the PHY digital waveforms representing the modulated bits. The digital waveforms are then transmitted to the ultrasonic transducer that converts the electrical signal to ultrasonic signal and radiates it in the communication channel.

Raw information bits from the host are received at the Tx controller, which coordinates the PHY layer operations implemented by the other blocks of the chain. The UsWB packet is then serialized, i.e., converted into a sequence of bits, and forwarded to the next module in the chain, i.e., Symbol Mapping. In the Symbol Mapping block the information bits are mapped into $\{-1,1\}$ binary symbols. The binary symbols are then spread in chips by the Spreading Code module following a pseudo-random spreading code. For each symbol, this block outputs M chips in $\{-1,1\}$. Chips are then forwarded to the Time-Hopping module that spreads them in time according to the selected time-hopping pattern. The time-hopping pattern is generated locally using a Linear Feedback Shifter Register (LFSR) module. Finally, the Pulse Shaping module maps the incoming chips to position-modulated pulses. The output is a train of position-modulated pulses following a predefined time-hopping pattern. Each pulse consists of three cycles of a 700 kHz square wave. A longer electrical excitation gives higher output pressure because of the resonant operation of the transducers. However, longer pulses lower the data rate. In some embodiments, three cycles can provide a good compromise between data rate and ultrasonic generation efficiency. In some embodiments, each packet is preceded by two preambles. The first preamble consists of 64 cycles of a 700 kHz sine wave and it is used at the receiver for packet detection, i.e., coarse synchronization. The second preamble consists of a train of three pulses properly spaced in time, and it is used for achieving time-hopping synchronization, i.e., fine synchronization.

Rx Chain Design.

In some embodiments, the receiver chain can implement the receiver UsWB PHY layer functionalities. The received ultrasonic signal is converted to an electrical signal by the Rx transducer. The signal is amplified by the LNA, and analog-to-digital converted by the ADC. Then, the receiver chain in the FPGA processes the digital waveform acquired through the SPI Master module. The receiver chain outputs a binary stream representing the received decoded data, which are delivered to the MCU through the SPI Slave module. The Rx controller coordinates the PHY-layer processing of the received digital waveform. In some embodiments, the Rx controller can trigger the start of the PHY layer processing when synchronization is achieved, and make the decision of the received bits based on the output of the PHY layer processing blocks. The Rx controller can also be in charge of switching the ADC in from power-down mode to power-up, and vice versa. The preamble detectors include a packet detector and a time-hopping synchronization block. The former enables coarse synchronization by identifying an incoming packet using an energy collection approach, which aims to detect the sine wave preamble. The latter identifies the exact start point of the time-hopping frame by correlating the received signal with a local copy of the transmitted pulse-train preamble. After synchronization is achieved, the time-hopping deframer jumps from frame to frame and feeds to the pulse correlator block only the time slots in which a pulse is expected according to the time-hopping sequence in use. The time-hopping sequence can be generated using a linear feedback shift register (LFSR) module that uses the same seed as the LFSR of the transmitting node. The pulse correlator correlates and integrates the signal in each time slot and outputs a positive value for a slot containing a '1' symbol, and a negative value for a slot containing a '−1' symbol. The correlation output goes into the code despreader, which inverts the spreading operation by weighting the correlation output with the spreading code originally used at the transmitter and summing these over the spreading code length. Based on the result of the despreading operation, the Rx controller makes a decision on the received bits. If the resulting sum is positive a 0-bit is received, otherwise a 1-bit is received.

Register Manager.

In some embodiments, a register manager can be in charge of storing and routing the configuration parameters written by the LL module running on the MCU on a pool of setting registers implemented on the FPGA. Through these setting registers, one can reconfigure key parameters of the PHY layer transmission scheme (i.e., frame and code length, among others). Whenever the driver reconfigures any parameter, the register manager stores the received data in the desired register and routes this parameter to the destination module. This block enables real-time reconfiguration thus enhancing the transceiver flexibility. The communication system can allow real-time reconfiguration of several parameters, i.e., spreading code and spreading code length, time-hopping frame length and time-hopping sequence, packet payload size, and length of the preambles.

SPI Module.

In some embodiments, the FPGA can include a configurable serial peripheral interface module. For example, the iCE40 Ultra FPGA has two SPI hardened, i.e., already fabricated in the FPGA, IP cores. The hardened cores are accessible through a system bus that provides connectivity between FPGA user logic and the hardened IP blocks. The user can configure the cores to operate as master or slave, and can configure the SPI communication settings, e.g., data rate, clock polarity and clock phase, among others. In some embodiments, the SPI interfaces enable communication with the external peripherals and the MCU. In some embodiments, one hardened SPI core can be configured as slave, and one as master. The SPI Slave block is driven by the SPI Master module of the MCU. This SPI link is used to pass the data to be transmitted to the FPGA, and to read the received data from the FPGA. Moreover, the MCU can use this serial link to deliver to the register manager PHY layer parameters. The data rate on this link needs to be greater than the PHY layer data rate, such that the PHY Tx chain is always backlogged with byte to transmit. In some embodiments, a 1 MHz SPI clock can be used. The SPI Master block can drive the communication with the ADC. For example, the SPI Master can trigger the sampling operations on the ADC, and read back the sampled digital waveform. As discussed in Section II-A2 above, to support 2 MHz sampling rate, the SPI Master link can be clocked at 32 MHz.

FIFOs.

In some embodiments, FIFO blocks can implement first-in-first-out memory queues that allow the storage and retrieval of ordered data. In one embodiment, FIFO blocks can buffer data coming in and out of the FPGA from and to the external peripherals and the MCU, before being processed by the functional logic. FIFOs can also be used to handle multi-clock domain data exchange, i.e., data flowing between logics driven by clock signals with different frequencies.

PLL Module.

In some embodiments, the FPGA can include a Phase Locked Loop (PLL) module to provide a variety of user-synthesizable clock frequencies, along with custom phase delays, to support multi-clock domain designs. For example, the iCE40 Ultra FPGA includes an ultra-low power Phase Locked Loop. The PLL can be used to internally synthesize the 32 MHz clock signal to individually drive the SPI Master block to minimize dynamic power consumption, which is proportional to the circuit clock frequency. The PLL module can be shut down when communication with the ADC is not needed to minimize the energy consumption.

FPGA Resource Utilization.

The FPGA includes programmable logic blocks (PLBs) that can be programmed to perform logic and arithmetic functions. Table I reports the FPGA resource utilization of the iCE40 device for the modules discussed above in terms of programmable logic blocks (PLBs), and resource percentage. Each PLB includes eight interconnected logic cells (LC), and each LC contains one look-up table (LUT) and one register. In some embodiments, the ICE40 Ultra FPGA contains 440 PLBs, i.e., 3, 520 LC.

TABLE I

Resource occupation of the logic implemented on the on the FPGA.

| Module | PLBs | % |
| --- | --- | --- |
| SPI Slave | 61/440 | 14% |
| Tx Logic | 44/440 | 10% |
| SPI Master | 82/440 | 18% |
| Rx Logic | 252/440 | 57% |
| Tot | 439/440 | 99% |

The receiver logic occupies more than 50% of the available resources on the FPGA. To bring down the total FPGA utilization below 100%, the synchronization process can be simplified and optimized. In particular, the correlator templates used for synchronization can be square-shaped waveforms of amplitude '−1' and '1', instead of sine wave templates which match the received signal. As a consequence, the template can be implemented using 2-bit coefficients instead of 12-bit coefficients (same size as the input).

Figure 8:
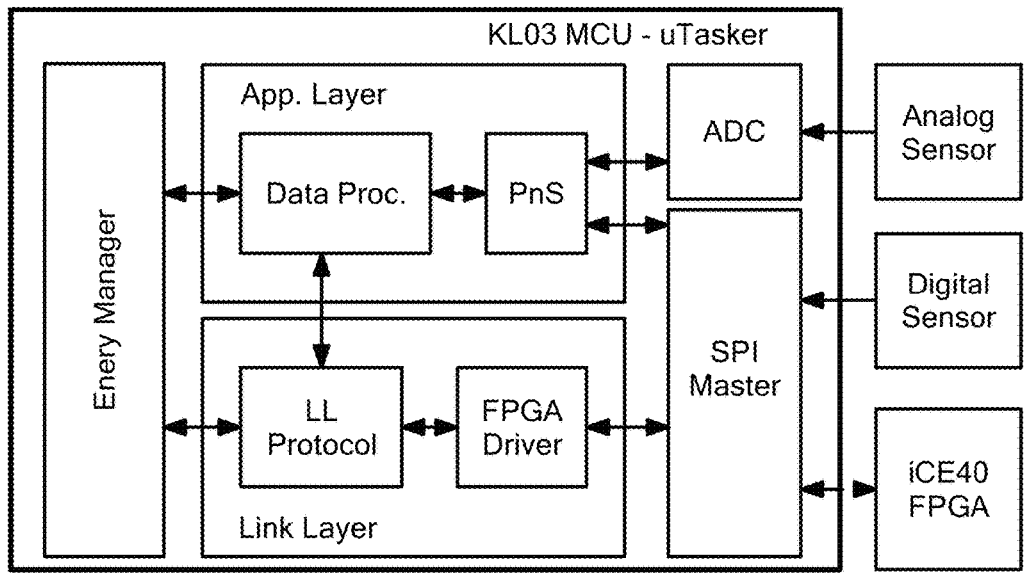
FIG. 8 is a schematic block diagram of an embodiment of MCU firmware architecture employing a KL03 MCU.

2) Core MCU Firmware: In some embodiments, the MCU software architecture can be implemented on a real-time operating system (RTOS) to ease the development of complex software functionalities, e.g., timers and interrupts for sensing and transmitting data. In one embodiment, an μTasker embedded RTOS was implemented, which can run in a resource constrained environment such as the Freescale KL03 MCU and offers support to the MCU low-power functionalities. μTasker is suited for embedded applications where tight control over resources is desired. FIG. 8 shows the firmware architecture implemented on the KL03 MCU. In one embodiment of an application scenario, the application layer can trigger a reading through the PnS interface from a digital or analog sensor. The sensor reading is then processed by the reconfigurable data processing functionalities and passed to the LL protocol module for transmission. The LL packet is passed to the FPGA driver module that transmits the data to the FPGA through the SPI Master interface. In parallel, the energy manager module can be in charge of switching between different energy states to minimize the system energy consumption.

Link Layer.

In some embodiments the UsWB Link Layer (LL) protocol can be in charge of managing the data transmission over the UsWB PHY layer interface. The connection is established through an advertising process initiated by a first node, i.e., the slave, which transmits periodically advertising packets on an advertising channels. The advertising channel is implemented using a common and known-a-priori time-hopping sequence and spreading code. Data channels are implemented using unique and private time-hopping sequences and spreading code pairs shared between the two communicating nodes. The time interval between advertising packets can be a fixed delay plus a random delay that reduces the possibility of collisions between advertisements of different devices. The advertising interval can be selected to find a compromise between energy consumption and delivery delay. A long interval allows saving of power, but at the same time significantly slows down the data exchange operations.

A second node, i.e., the master, scans the advertising control channel, and upon receiving an advertising packet, sends a connection request to the slave and they agree on a connection interval between connection events in which the two nodes exchange data periodically. During a connection event, both the slave and the master wake up, and the slave transmits a data packet. Since the sleep clocks of the slave might drift away from the sleep clock of the master, the slave starts listening on the radio channel slightly before the agreed connection interval.

In some embodiments, the UsWB LL packet can include a 2-byte header, a 3-byte CRC, and a variable size payload between 0 and 32 bytes. The header can include a 2-bit packet type field, i.e., advertising, connection request and data packet, 5-bit payload length, 3-bit Tx address, 3-bit Rx address, 1-bit SN (sequence number), 1-bit NESN (next expected sequence number) and 1-bit MD (more data). The LL packet can be preceded by the two synchronization preambles used for coarse and fine synchronization. The connection can use a stop-and-wait flow control mechanism based on cumulative acknowledgments, with error recovery capabilities as used in BLE LL protocols. The SN bit identifies the packet, while the NESN indicates the next expected packet from the other device. If a device successfully receives a data packet, it increments the NESN of its next packet, serving as an acknowledgment. Otherwise, the receiving device retransmits the last transmitted packet, which serves as a negative acknowledgment. A More Data (MD) bit indicates that the device has more data to send in the same connection event.

In some embodiments, the link layer can also implement driver functionalities for the for the UsWB transceiver implemented on the FPGA that allows initializing the transceiver, configuring PHY layer parameters and triggering the transmitting and receiving operations. When data needs to be transmitted or received, the MCU can enable the FPGA operations, configure parameters such as code and frame length, among others, and pass the data to be transmitted or wait for the received data. This data exchange can be done through a SPI link between the MCU (master) and FPGA (slave), and the register manager on the FPGA can be in charge of storing and using the information received.

Application Layer.

In some embodiments, at the application layer, the MCU firmware can implement the Plug-n-Sense (PnS) software module that allows the IoMT-mote to connect with different sensing devices. The PnS module can include a digital interface based on I2C/SPI Master interfaces that can directly connect to sensors with digital output, as well as an analog interface based on the 12-bit embedded ADC that can sample and digital-convert the output of analog sensors. Data coming from the PnS module are then processed by the reconfigurable and modular data processing module implemented in the MCU. Each sensor data is mapped into a content object and advertised to make it reachable from the IoMT-patch. The IoMT-patch maps the content object to the LL address of the IoMT-mote generating the object, and therefore retrieves the information whenever needed. Application layer data can be encrypted end-to-end using a streamlined implementation of the Advanced Encryption Standard (AES) based on a 128 bit key exchanged during paring between two devices.

In some embodiments, the data processing module can be based on decomposing the data processing applications running in the IoMT-mote into primitive blocks, and offering real-time reconfigurability at the application layer. The processing application can include a sequence of basic operations that are executed on the sensed data to extract desired medical parameters. Real-time modular reconfiguration allows new processing functions to be wirelessly transmitted and installed on the IoMT-platform at runtime, such that new medical parameters can be extracted from the raw data coming from a sensor device, while maximizing code reusability. Defining new applications can include specifying inputs, a chain of primitive blocks, and outputs. An input is the digital or the analog interface of the PnS module, thus the sensor device attached to it, e.g., an electrocardiogram (ECG). An output can be either the local memory for storing a measured parameter, or a transmission for sending a measured parameter to another IoMT-mote or IoMT-patch.

Figure 9:
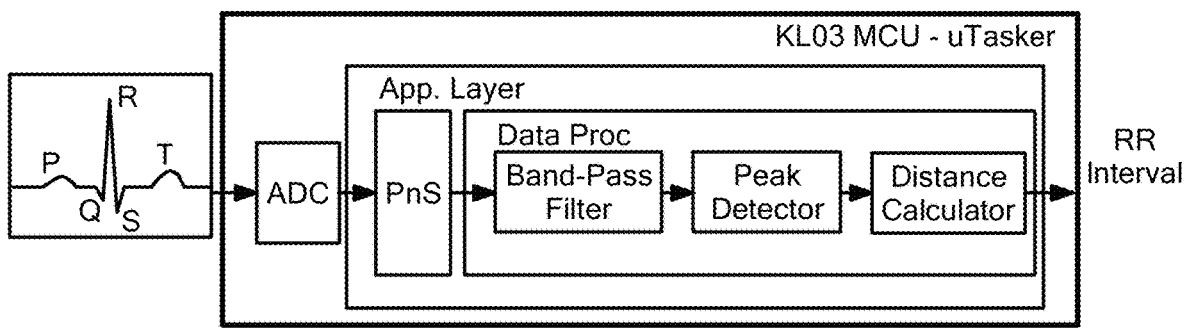
FIG. 9 is a schematic diagram of an embodiment of primitive blocks of a heart rate monitor.

Based on this modular approach, applications can be represented by chains of binary sequences, i.e., keys. Each primitive function is mapped to a binary key. A concatenation of keys represents a concatenation of operations, and therefore represents an application. The IoMT-mote feeds these keys into a finite state machine (FSM) where each state represents a primitive block function. By parsing the consecutive function keys, the FSM transitions from state to state, processing inputs and producing outputs. In one example, an ECG-based application measures the heart rate from a single electrode ECG signal coming from the PnS interface. FIG. 9 shows a template signal with five labeled characteristic waveforms that correspond to electrical events during one heartbeat, and present the simplified primitive block sequences of the heart rate detector. The application measures the heart rate in beats-per-minute (bpm) by dividing 60 for the average of the RR interval duration, i.e., distance between two consecutive R waveforms in the trace.

A variety of sensor devices can be used, for example and without limitation, a motion sensor, a gyroscope, an accelerometer, a cardiac rhythm monitor, a heart rate monitor, a pulse monitor, a blood pressure monitor, a glucose sensor, a drug pump monitor, a sleep sensor, a REM sleep duration sensor, a still camera, a video camera, a sensor for one or more biomolecules, a sensor for one or more pharmaceutical agents or pharmaceutical formulation ingredients, a sensor for a dissolved gas or ion, and a sensor for pH, ionic strength or osmolality. Similarly, a variety of actuating devices can be used, for example and without limitation, a drug pump, a heart stimulator, a heart pacemaker, a bone growth stimulator, a deep brain stimulator, a neurostimulator, and a neuromuscular electrical stimulator.

Energy Manager.

By leveraging µTasker RTOS primitives to enter and exit the KL03 MCU power modes through interrupts generated by timers or external pins, software functionalities can be implemented to minimize the system energy consumption. In some embodiments, an energy management module can be provided to do one or more of the following: (i) adjust at runtime the core clock frequency according to the processing power required, (ii) select at runtime the low-power mode according to the application requirements, (iii) implement automatic wake-up functionalities, and (iv) power up and shut down other components in the system to further reduce the system power consumption.

In some embodiments, in RUN mode the MCU operates at its maximum performance and consumes, in one example, around 6.6 mA at 48 MHz. Every time there are no tasks scheduled, the µTasker RTOS switches automatically to a low-power mode. By default, the MCU goes into WAIT mode where all the peripherals function while the core is in Sleep mode, reducing the current drawn to 1 to 1.4 mA. As soon as a task is scheduled, an internal interrupt brings the MCU back to RUN mode. When less processing power is needed in RUN mode, e.g., when the MCU just reads and stores sensed information, the clock frequency can be reduced to lower the power consumption. For example, the MCU draws 1.8 mA and 1 mA when under-clocking the system to 3 MHz in RUN and WAIT mode, respectively. In STOP mode, the MCU goes to deep sleep and all the peripheral clocks are stopped and the chip goes static state bringing the current drawn down to 160 µA. In VLPS mode more peripheral are put to sleep and the current drawn is further reduced to 2.2 µA. In STOP and VLPS mode the nested vectored interrupt controller (NVIC) is disabled, and therefore the scheduler interrupts do not awaken the MCU. Instead, an asynchronous wake-up interrupt controller (AWIC) can be used to wake up from timers or pin interrupts. Finally, in very-low-leakage stop (VLLS) mode, all the peripherals including the RAM are shut off, bringing the current drawn down to 0.6 µA. In VLLS1 mode the processor can be awakened using a low-leakage wakeup unit (LLWU) that enables timers, e.g., the LPTMR clocked by the low-power oscillator (LPO), to be programmed as wakeup sources.

To reduce the energy consumption of the entire system when idle, the energy manager module can be in charge of powering up the system components only when needed. For example, the ADC is used only when the device is receiving; the FPGA running the PHY layer functionalities can be used only when information has to be transmitted or received. In some embodiments, with the MCU in VLLS1 mode and the rest of the system powered down, the device can consume less than 1 µA when not in use.

III. IOMT-PATCH DEVICE

The IoMT-patch device, which may also be termed a wearable device or a gateway device or node, is deployed along a body to bridge the intra-body network of implantable node with the external world. The IoMT-patch devices can also accommodate sensing capabilities if required, e.g., electrocardiogram leads.

The IoMT-patch device hardware design can be similar to the IoMT-mote device hardware design except for a few different components. The IoMT-patch device can be a flexible sensing/processing/networking platform with a small and compact form factor, e.g., no more than two centimeters per side in some embodiments, that can offer low energy consumption, and that communicates wirelessly through ultrasounds and RF. The gateway node can be packaged such to offer a slim form factor that can be attached to stick-on skin patches.

The hardware architecture of the IoMT-patch device can be similar to one of the IoMT-mote device discussed above. The hardware design of the IoMT-patch device can be based on mm-sized and low-power field programmable gate arrays (FPGAs) or/and microcontroller units (MCUs) that offer hardware and software reprogrammability in small packages and low energy consumption. The IoMT-patch device can optionally offer sensing capabilities for measuring biomedical parameters measurable on the body surface, e.g., ECG signals. The communication through ultrasounds, both with the IoMT-mote device in body tissues and with an access point node in air, can be done by using miniaturized piezo-electric transducers. For example, in some embodiments, the IoMT-patch device can embed two arrays of miniaturized ultrasonic transducers that offer high integration, as well as focusing and beamforming capabilities that enhance the ultrasonic propagation in body tissues and in air. The two arrays are differently coupled with the external medium to support communication in air and in body tissues, respectively. The IoMT-patch device also can embed a low-power RF transceiver that enables communication via RF with the access point node. The IoMT-patch device is powered by a small and thin rechargeable battery that can be recharged after detaching the device from the body. The IoMT-patch device can also provide human energy harvesting or ultra-sonic wireless energy transfer functionalities that help prolonging the device battery life.

The communication interface enables ultrasonic wireless connectivity through data converters, power and low noise amplifiers, and transducers. In some embodiments, the communication interface can include two receiver (Rx) and two transmitter (Tx) chains. The Rx chains can include a low-noise amplifier and an analog-to-digital converter (ADC) to amplify and digital-convert the received signals. The Tx chain can include a digital-to-analog converter (DAC) and a power amplifier to analog-convert and amplify the digital waveforms before transmission. Tx and Rx chains can be in charge to transmit and receive data through the ultrasonic transducers. The first Tx/Rx chain pair is used for the in-tissue communication with the IoMT-motes, while the second Tx/Rx chain pair is used for the in-air communication with access point nodes. The communication between the core unit and the communication interface can be performed through serial or parallel communications.

The IoMT-patch devices can also embed a low-power RF transceiver that enables communication via RF with access point nodes. In some embodiments, the RF chip can operate in the industrial, scientific and medical (ISM) radio band as well as in the Medical Implant Communication Service (MICS) band. The RF chip can implement wireless short range or local area network communication standards, such as Bluetooth, Wi-Fi or ZigBee, as well as proprietary communication schemes and protocols.

The IoMT-patch device includes a power unit that can accommodate a battery element to power the device. The power unit of the IoMT-patch device can also embed a ultrasonic power transmission unit to wirelessly transfer ultrasonic energy to the implantable nodes.

In some embodiments, an IoMT-patch device can be based on the same hardware and software implementation of the IoMT-mote device presented above in Section II, with the exception of the KL03 MCU, which can be replaced with a wireless MCU that embeds the RF interface required in the IoMT-patch to bridge the on-body system with the access point. In some embodiments, an access point device can include a multi-platform smartphone app that communicates via BLE with the IoMT-patch and gives the user direct access to the sensed data. In some embodiments, an access point device can include a 6LOWPAN edge router implemented on a traditional computer or on single-board computer, e.g., Raspberry Pi, that enables IPv6 connectivity and allows direct data delivery to the cloud. In the following, an IoMT-patch implementation is described, focusing on the modules that differ from the IoMT-mote implementation described above.

A. MCU and RF Interface

In some embodiments, the IoMT-patch can embed a wireless MCU, such as TI CC2650 BLE MCU, that coordinates transmissions over the ultra-sonic interface, as discussed in Section II-A1, and transmissions over the RF interface, and implements upper layer protocols to interface the system with the access point device, e.g., a smartphone or the a 6LoWPAN edge router. The TI CC2650 MCU is a commercially available low power (between 6 mA and 9 mA in Tx/Rx mode) and small (down to 4×4 mm) 2.4 GHz wireless MCU that can operate in energy constrained systems powered by small coin cell batteries. The CC2650 device contains a 32-bit ARM Cortex-M3 processor running at up to 48 MHz that implements upper layers of the BLE protocol stack, as well as user defined functionalities. A secondary low-power ARM Cortex-M0 processor is in charge of lower-level BLE functionalities and is interfaced with the embedded RF transceiver. For one embodiment, the SmartRF development kit provided by the vendor was used, which includes all the hardware and software tools needed to test the radio performance and implement software operations B. Software Implementation In some embodiments, two different firmwares for the wireless MCU, e.g., the TI CC2650, can be implemented. In some embodiments, a BLE-enabled firmware based on TI-RTOS that implements BLE functionalities for connecting the patch to the BLE access point, e.g., a smartphone. In some embodiments, a IPv6-enabled firmware, such as that based on the Contiki operating system that offers 6LoWPAN capability for IPv6 support and connects to the 6LoWPAN edge router. Alternatively, a single-solution RTOS that support both BLE and 6LoWPAN could be used. A BLE-enabled access point can be implemented through a multi-platform smartphone app that collects sensed data and presents them to the user and a 6LoWPAN edge router example running on a Raspberry Pi that collect the data and publish them on a cloud service via MQ Telemetry Transport (MQTT) protocol.

1) BLE-enabled Firmware: For the BLE-enabled firmware, in some embodiments, the RTOS from TI can be used, which offers preconfigured and easy to use drivers for accessing the system peripheral, e.g., SPI/I2C, managing the RF interface and provides easy access to the BLE protocol stack library available on the device, as well as control of the power management of the device. The BLE interface can implement functionalities for establishing the connection between the IoMT-patch and the BLE access point and exchange of data between the two devices. The connection operations can be managed by the Generic Access Profile (GAP) layer of BLE. The connection can be established through an advertising process initiated by the slave, i.e., the IoMT-patch, which transmits periodically advertising packets on three control channels. In some embodiments, the advertising time can be set to 300 ms which is a good tradeoff between energy consumption and user experience. A long interval allows saving power, but at the same time significantly slows down the connection operations. When the master, i.e., the BLE access point, receives an advertising packet, it sends a connection request to the slave and they agree on a connection interval between connection events in which the two nodes exchange data periodically. In some embodiments, the connection interval can be set to 2 s. When no more data needs to be exchanged the connection is closed and the slave goes back to advertising mode.

In some embodiments, data exchange between connected devices can be managed by the General Attribute (GATT) layer of the BLE protocol stack, and data can be exchanged in form of characteristics. Characteristics can be grouped in services, and services can be grouped in profiles. For example, in this implementation, consider a heart rate profile, which includes a Heart Rate Service and a Device Information Service, and contains a Heart Rate Measurement that the access point wants to retrieve from the IoMT-patch. In the background, the IoMT-patch initializes the ultrasonic intra-body communication to retrieve the heart rate measurement from the IoMT-motes. Each BLE characteristic corresponds to one content object that is mapped to the LL address of the IoMT-mote that offers the object. During the over-the-air data exchange, the communication is hard to eavesdrop because of the frequency-hopping scheme adopted by the BLE physical layer. Moreover, the GATT layer can offer data protection through end-to-end encryption, authentication and authorization processes.

Figure 10:
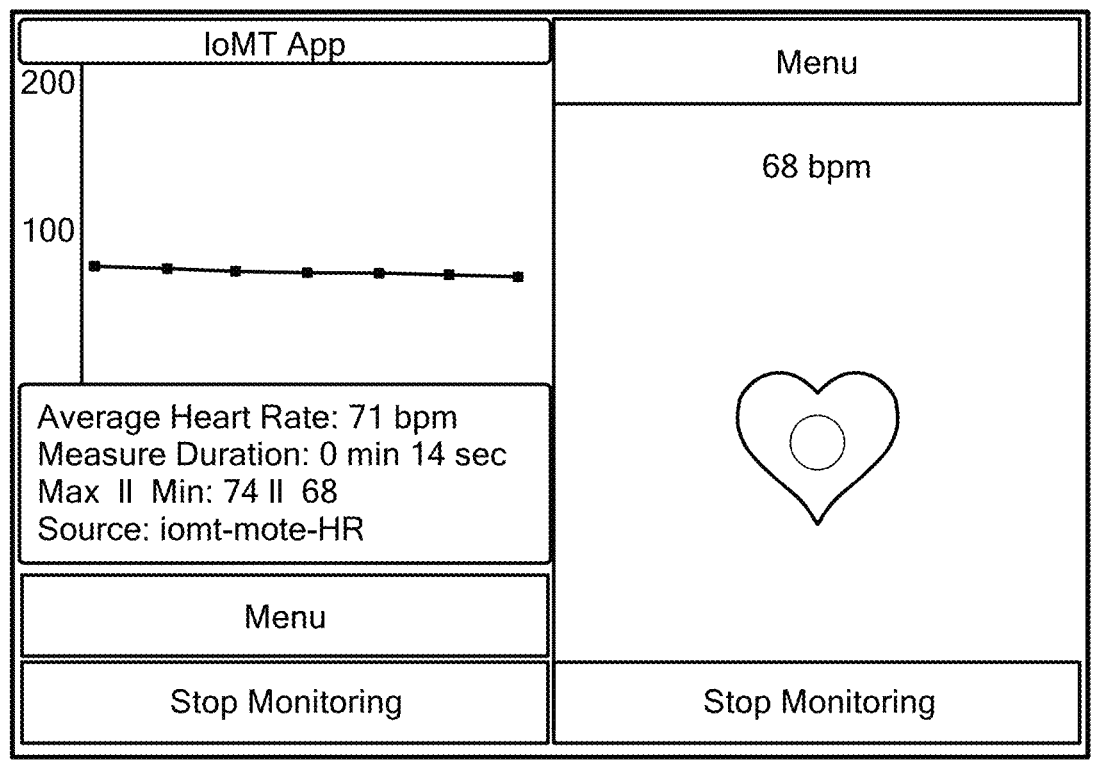
FIG. 10 is an embodiment of a screenshot of a BLE app GUI.

2) BLE-enabled Access Point: In some embodiments, a smartphone app can be based on the Qt framework, which offers a set of easy-to-use libraries to develop multiplatform application and user interfaces. For example, in some embodiments, the app can implement a simple BLE heart listener that scans for BLE devices, connects to the Heart Rate service running on the IoMT-patch and retrieves and presents to the user the heart rate measurement. The app can use the Qt BLE API that provide high level access to BLE drivers available on different platform. Currently Qt BLE API supports Android, iOS, Linux (BlueZ 4.x/5.x) and OS X. FIG. 10 shows two example screenshots of an app graphic user interface (GUI) compiled for Android. Through the GUI the user can trigger a reading from the IoMT-patch and visualize the heart rate measurement.

3) IPv6-enabled Firmware: In some embodiments, for the IPv6-enabled firmware, the Contiki OS can be used, which is designed for low-power wireless Internet of Things devices. Contiki supports the 6LoWPAN standard, which offers encapsulation and header compression mechanisms that allow IPv6 packets to be sent and received over IEEE 802.15.4 based wireless mesh network networks. Using 6LoWPAN, the IoMT-patch can have its own IPv6 address, allowing it to connect directly to the Internet using open standards. An edge router, i.e., a gateway between the 6LoWPAN mesh and Internet, can be used to provide a conversion between 6LoWPAN and standard IP header. In some embodiments, the IoMT-patch can be configured as a Message Queue Telemetry Transport (MQTT) client that periodically reads data from the IoMT-mote through the ultrasonic interface, and publishes sensor readings to an MQTT broker, i.e., the server responsible for distributing messages. The MQTT client module can be responsible for opening the connection with the MQTT broker through an IPv6 address, authenticating the application, and publishing new content when available. As an example, the device can be set up to publish readings to IBM Watson IoT Platform quick start service and visualize the sensor readings together with the device uptime in seconds and the message sequence number.

4) 6LOWPAN Edge Router: An edge router, i.e., a gateway between the 6LoWPAN mesh and Internet, can be used to provide a conversion between 6LoWPAN and standard IPv6 header. In some embodiments, the edge router can be implemented using the CETIC 6LBR 6LoWPAN Border Router solution. The 6LBR is deployment-ready and can be easily configured to interconnect 802.15.4/6LoWPAN networks with an existing IPv6 network. The 6LBR can be run on, for example, a Raspberry Pi connected with an TI CC2531 that provide the 802.15.4 radio interface, and with the Internet through the Ethernet interface.

The IoMT architecture platform and wirelessly networked systems of implantable and wearable medical devices endowed with sensors and actuators as described herein can be used for many therapies. The platform and devices can be used with artificial pancreases, i.e., implanted continuous glucose monitors wirelessly interconnected with adaptive insulin pumps, for many type-1 diabetic patients. Post-surgery sensors can be used to detect changes in the microenvironment involved with the surgical procedure (pressure, pH, white cells concentration, LDH enzyme) to prevent infections or ischemias caused by tissue perfusion. Other applications include functional electrical stimulation, a type of neurostimulation to restore motion in people with disabilities by injecting electrical currents to activate nerves innervating extremities affected by paralysis. Neurostimulators can be composed of several miniaturized standalone stimulation devices that attach to different groups of neurons and wirelessly cooperate with each other to modulate the electrical signaling patterns to restore the healthy states of targeted organs and functions. Distributed pacemakers can include sensing and pacing devices implanted in the heart chamber connected wirelessly with each other to enable advanced cardiac resynchronization therapy.

The sensor and/or actuating unit can employ a variety of sensors to sense biological parameters or actuators to actuate biological or medical procedures.

In some embodiments, a sensor can comprise a motion sensor, a gyroscope, an accelerometer, a cardiac rhythm monitor, a heart rate monitor, a pulse monitor, a blood pressure sensor, a glucose sensor, a drug pump monitor, a sleep sensor, a REM sleep duration sensor, a still camera, a video camera, a sensor for one or more biomolecules, a sensor for one or more pharmaceutical agents or pharmaceutical formulation ingredients, a sensor for a dissolved gas or ion, or a sensor for pH, ionic strength or osmolality.

In some embodiments, the sensor for one or more biomolecules can comprise a sensor for one or more peptides, oligopeptides, polypeptides, proteins, glycoproteins, antibodies, antigens, nucleic acids, nucleotides, oligonucleotides, polynucleotides, sugars, disaccharides, trisaccharides, oligosaccharides, polysaccharides, lipids, glycolipids, proteolipids, cytokines, hormones, neurotransmitters, metabolites, glycosaminoglycans, and proteoglycans.

A motion sensor can determine vibration, position, velocity, and acceleration by any active or passive means known in the art, such as by emitting and receiving infrared, microwave and/or ultrasonic radiations.

A gyroscope can allow the calculation of orientation and rotation, while an accelerometer can measure non-gravitational acceleration. A gyroscope and an accelerometer can be used separately, or they can be combined to create an inertial measurement unit to provide exact information on orientation, position, and velocity.

A cardiac rhythm monitor can detect abnormal or irregular heart rhythms, such as those caused by atrial or ventricular fibrillation, conduction disorders or other arrhythmias. A heart rate monitor can measure the number of heart contractions per unit of time. A pulse monitor can measure the heart rate as felt through the walls of a peripheral artery. A blood pressure sensor can measure systolic, diastolic and mean arterial pressure.

A glucose sensor can provide discrete or continuous measurement of blood glucose levels.

A drug pump monitor can monitor the dosage and rate of administration of one or more agents by one or more drug pumps.

A sleep sensor can simultaneously track a number of indicators related to the quantity and quality of sleep, such as brain activity, eye movements, heart rate, muscle tension, oxygen levels, breathing abnormalities and snoring. A sleep monitor can therefore encompass multiple tests and/or devices, including electroencephalograms, electrooculograms, electrocardiograms, electromyogram, oximeters, breathing sensors and microphones. A REM sleep duration sensor can detect and quantify the period of a user's sleep that is REM (rapid eye movement) sleep. REM sleep can be detected by measuring eye movement during sleep using electrooculography, an infrared camera, or any other method known in the art.

A still camera can be used to capture and/or record images of one or more tissues of a user. A video camera can be used to capture and/or record sequences of images of one or more tissues of a user constituting videos or movies. The still or video cameras can be of any suitable modality, including visible light and infrared cameras.

A sensor for one or more pharmaceutical agents or pharmaceutical formulation ingredients can be a sensor for monitoring the systemic or local levels of a pharmaceutical agent or ingredient. The sensor can be used to monitor agents that have a narrow therapeutic range, that exhibit high pharmacokinetic variability or to test novel pharmaceutical compounds. For example, the sensor can be a sensor for flecainide, procainamide, digoxin, phenytoin, lithium, valproic acid, gentamicin, amikacin, tacrolimus and/or theophylline.

A sensor for a dissolved gas or ion can be used to measure the local or systemic levels of gas or ions present in one or more tissues. The gas sensor can detect the levels of any gas of interest, such as partial oxygen and carbon dioxide pressures, and nitric oxide levels, thus detecting hypoxia or other conditions. The ion sensor can measure the levels of any relevant ions, such as sodium, potassium, calcium, phosphate, zinc, and iron, thus detecting hyper- or hyponatremia, hyper- or hypo hypokalemia, anemia, or other conditions. A pH sensor can specifically detect hydrogen ions and thus detect acidosis or alkalosis. An ionic strength sensor can measure the concentration of ions in a solution, and an osmolality sensor can measure the body's electrolyte-water balance. Alone or combined, the aforementioned sensors can detect a variety of physiological and pathological states according to the gas and solute concentration in a tissue, including apnea, dehydration, heart and kidney disease, and diabetes.

All of the above mentioned sensors can detect changes in real time and/or record data for later retrieval and analysis.

In some embodiments, the actuator can comprise a drug pump, a heart stimulator, a heart pacemaker, a bone growth stimulator, a deep brain stimulator, a neurostimulator, or a neuromuscular electrical stimulator.

A drug pump can be used to control the dosage and rate of local or systemic administration of one or more agents.

A heart pacemaker can be used to deliver electrical impulses to the heart in order to regulate heart rhythm and rate. A pacemaker can also be combined with a defibrillator. A heart stimulator can be programmed to deliver stimulatory impulses to the heart in any specified frequency and to any specified region.

A bone growth stimulator can be used to assist in any osteogenesis process. A bone growth stimulator can be used to accelerate healing of bone fractures, fusions, or delayed unions by any method known in the art, including via electric or ultrasonic stimulation.

A neurostimulator can used to deliver electric stimulation to targeted brain areas in order to interfere with neural activity at the target site. A neurostimulator can be used to increase or decrease neuronal activity at the site of interest. A neurostimulator can be a deep brain stimulator.

A neuromuscular stimulator can be used to deliver electrical stimulation that simulate the action of the central nervous system on muscles. A neuromuscular stimulator can be used, for example, to improve or recover muscle function, and for chronic pain management.

In some embodiments, a system can be provided. In some embodiments, a system can include an RF/ultrasound communication device as described herein, one or more ultrasound communication devices implantable within a body and capable of ultrasound communication with the communication device. In some embodiments, the RF/ultrasound communication device can be worn on a skin surface of a body and the one or more ultrasound communication devices are implanted within the body. In some embodiments, an access point device, including a communications interface can be operative to receive and transmit radio frequency transmissions with the RF/ultrasound communication device. In some embodiments, one or more sensing devices can be a motion sensor, a gyroscope, an accelerometer, a cardiac rhythm monitor, a heart rate monitor, a pulse monitor, a blood pressure monitor, a glucose sensor, a drug pump monitor, a sleep sensor, a REM sleep duration sensor, a still camera, a video camera, a sensor for one or more biomolecules, a sensor for one or more pharmaceutical agents or pharmaceutical formulation ingredients, a sensor for a dissolved gas or ion, or a sensor for pH, ionic strength or osmolality. Each sensing device can be in communication with an ultrasound communication device of the system. In some embodiments, one or more actuating devices can be a drug pump, a heart stimulator, a heart pacemaker, a bone growth stimulator, a deep brain stimulator, a neurostimulator, or a neuromuscular electrical stimulator. Each actuating device can be in communication with an ultrasound communication device of the system.

In some embodiments, a method can be provided. In some embodiments, a method can A method of controlling a plurality of networked medical devices, the method include providing a system as described herein including one or more sensing devices and/or one or more actuating devices, each in communication with an ultrasound communication device of the system; configuring the protocol stack and logic device of each ultrasound communication device in the system; acquiring data from the one or more sensing devices and optionally processing the data; optionally communicating the data using the RF/ultrasound communication device, an access point, and the internet to a physician; optionally receiving reprogramming instructions using the RF/ultrasound communication device, access point, and internet; reconfiguring the protocol stack and logic device of one or more selected ultrasound communication devices in the system in response to the reprogramming instructions; and optionally causing one or more of said actuating devices to change their actuation state.

In some embodiments, the reprogramming instructions can include altering one or more of a data acquisition rate, a data transmission rate, and a type of data sensed by one or more of said sensing devices. In some embodiments, the reprogramming instructions can include one or more of altering a parameter, a duty cycle, and a state of one or more of said actuating devices. In some embodiments, the reprogramming instructions can include altering one or more of a dosage and a rate of administration of one or more agents. In some embodiments, the reprogramming instructions can include altering an instruction to one or more of said sensing devices or said actuating devices in response to a feedback algorithm. In some embodiments, the reprogramming instructions can include altering an instruction to one or more of said sensing device or said actuating devices in response to a physiological or pathological state of a patient. In some embodiments, the reprogramming instructions can include triggering a reading from one or more of said sensing devices or said actuating devices and processing the reading. In some embodiments, the reprogramming instructions can include altering an instruction to adjust at runtime a core clock frequency according to a processing power requirement, select a low-power mode, provide an automatic wake-up, or power up or shut down instruction.

The system and method described herein can be used with humans and non-human animals and can be used in medical and veterinary fields.

The processing unit and communication unit described herein can be part of a computer system that executes programming for controlling the system for transmitting data ultrasonically among wearable devices as described herein. The computing system can be implemented as or can include a computing device that includes a combination of hardware, software, and firmware that allows the computing device to run an applications layer, including the application layer described above, or otherwise perform various processing tasks. Computing devices can include without limitation personal computers, work stations, servers, laptop computers, tablet computers, mobile devices, hand-held devices, wireless devices, smartphones, wearable devices, smart watches, smart clothing, embedded devices, microprocessor-based devices, microcontroller-based devices, programmable consumer electronics, mini-computers, main frame computers, and the like.

The computing device can include a basic input/output system (BIOS) and an operating system as software to manage hardware components, coordinate the interface between hardware and software, and manage basic operations such as start up. The computing device can include one or more processors and memory that cooperate with the operating system to provide basic functionality for the computing device. The operating system provides support functionality for the applications layer and other processing tasks. The computing device can include a system bus or other bus (such as memory bus, local bus, peripheral bus, and the like) for providing communication between the various hardware, software, and firmware components and with any external devices. Any other type of architecture or infrastructure that allows the components to communicate and interact with each other can be used.

Processing tasks can be carried out by one or more processors. Various types of processing technology can be used, including a single processor or multiple processors, a central processing unit (CPU), multicore processors, parallel processors, or distributed processors. Additional specialized processing resources such as graphics (e.g., a graphics processing unit or GPU), video, multimedia, or mathematical processing capabilities can be provided to perform certain processing tasks. Processing tasks can be implemented with computer-executable instructions, such as application programs or other program modules, executed by the computing device. Application programs and program modules can include routines, subroutines, programs, drivers, objects, components, data structures, and the like that perform particular tasks or operate on data. Real time responses can depend on the environment and the application or task being performed or updated. In some embodiments, can be on the order of seconds, milliseconds, or microseconds.

Processors can include one or more logic devices, such as small-scale integrated circuits, programmable logic arrays, programmable logic device, masked-programmed gate arrays, field programmable gate arrays (FPGAs), and application specific integrated circuits (ASICs). Logic devices can include, without limitation, arithmetic logic blocks and operators, registers, finite state machines, multiplexers, accumulators, comparators, counters, look-up tables, gates, latches, flip-flops, input and output ports, carry in and carry out ports, and parity generators, and interconnection resources for logic blocks, logic units and logic cells. Although certain embodiments are described above utilizing FPGAs, it will be appreciated that other logic devices, including programmable logic devices and application specification integrated circuits (ASICs) can be used in some embodiments.

The computing device includes memory or storage, which can be accessed by the system bus or in any other manner. Memory can store control logic, instructions, and/or data. Memory can include transitory memory, such as cache memory, random access memory (RAM), static random access memory (SRAM), main memory, dynamic random access memory (DRAM), and memristor memory cells. Memory can include storage for firmware or microcode, such as programmable read only memory (PROM) and erasable programmable read only memory (EPROM). Memory can include non-transitory or nonvolatile or persistent memory such as read only memory (ROM), memory chips, and memristor memory cells. Non-transitory memory can be provided on an external storage device. A computer-readable medium can include any physical medium that is capable of encoding instructions and/or storing data that can be subsequently used by a processor to implement embodiments of the method and system described herein. Any other type of tangible, non-transitory storage that can provide instructions and/or data to a processor can be used in these embodiments.

The computing device can include one or more input/output interfaces for connecting input and output devices to various other components of the computing device. Input and output devices can include, without limitation, keyboards, mice, joysticks, microphones, displays, touchscreens, monitors, scanners, speakers, and printers. Interfaces can include universal serial bus (USB) ports, serial ports, parallel ports, game ports, and the like. Other hardware components and devices can interface with the computing device. As used herein, the term "transceiver" can include one or more devices that both transmit and receive signals, whether sharing common circuitry, housing, or a circuit board, or whether distributed over separated circuitry, housings, or circuit boards, and can include a transmitter-receiver.

The computing device can access a network over a network connection that provides the computing device with telecommunications capabilities. Network connection enables the computing device to communicate and interact with any combination of remote devices, remote networks, and remote entities via a communications link. The communications link can be any type of communication link, including without limitation a wired or wireless link. For example, the network connection can allow the computing device to communicate with remote devices over a network, which can be a wired and/or a wireless network, and which can include any combination of intranet, local area networks (LANs), enterprise-wide networks, medium area networks, wide area networks (WANs), the Internet, cellular networks, and the like. Control logic and/or data can be transmitted to and from the computing device via the network connection.

The computing device can include a browser and a display that allow a user to browse and view pages or other content served by a web server over the communications link. A web server, server, and database can be located at the same or at different locations and can be part of the same computing device, different computing devices, or distributed across a network. A data center can be located at a remote location and accessed by the computing device over a network.

IV. EXAMPLES

Prototypes of the embodiments of the IoMT-mote and IoMT-patch described above were fabricated. In this section, a performance evaluation of the ultrasonic wireless interface implemented on the prototypes is presented in terms of communication reliability and energy consumption. The ultrasonic wireless interface was responsible for enabling communications between the IoMT-patch and the implanted IoMT-mote, and therefore its performance directly affected life-time of the implantable device, the most energy constrained device in the system. The ultrasonic wireless interface performance was also compared with the performance of an RF wireless interface based on the TI CC2650 BLE MCU when used for intra-body transmissions.

More particularly, the performance of the ultrasonic connectivity offered by the IoMT devices has been evaluated in terms of energy consumption and communication reliability using ultrasonic phantoms and porcine meat as communication media, and compared against state-of-the-art low-power RF-based wireless technologies operating in the unlicensed industrial, scientific, and medical (ISM) 2.4 GHz band, e.g., Bluetooth Low Energy (BLE). The ISM band is the RF band of choice for many future wireless medical devices. In fact, using standard technologies in the ISM band allows the interface of medical devices with commercial devices such as smartphones and tablets. Moreover, the ISM band offers larger bandwidth than other bands for medical applications, e.g., MedRadio, thus enabling a larger number of devices operating simultaneously. Also, the ISM band is internationally (un)regulated offering a larger market to medical device manufacturers. Because of the limitations of RF propagation in human tissue, RF-based technologies are not the best choice for intra-body communications, while ultrasonic waves offer higher reliability with much lower power transmission. For this reason, in the system architecture described herein, the use of RF-technology is limited to the out-the-body portion of the system. Specifically, it has been shown that ultrasonic waves can be efficiently generated and received with low-power and mm-sized components, and that despite the conversion loss introduced by ultrasonic transducers, the gap between RF and ultrasonic attenuation is still substantial, e.g., ultrasounds can offer 55 to 80 dB less attenuation than RF waves over 2 to 12 cm links and much lower energy consumption. Ultrasonic communications have been shown to require much lower transmission power compared to BLE with equal reliability, e.g., ultrasounds needs around 35 dBm lower transmission power over 12 cm communication distance for $10^{-3}$ BER leading to lower energy per bit cost and longer device lifetime. Finally, it has been shown experimentally that BLE links are not feasible at all above 12 cm, while ultrasonic links can achieve a reliability of $10^{-6}$ up to 20 cm with less than 0 dBm transmission power.

Example 1: Hardware Energy Consumption

Figure 11:
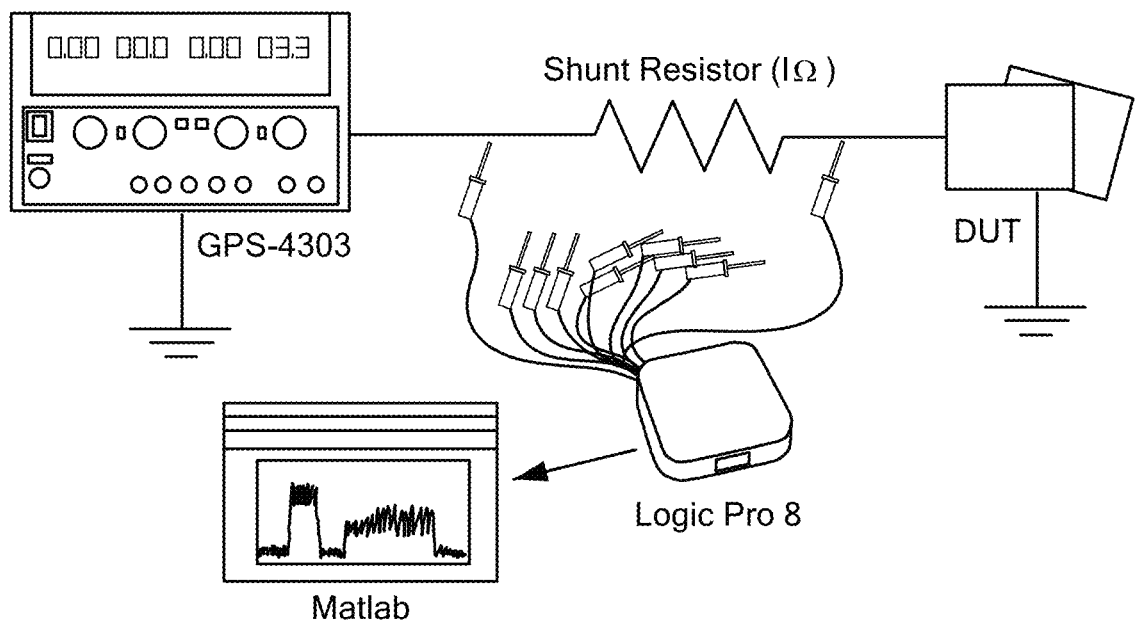
FIG. 11 is a schematic illustration of an embodiment of a current measurement setup.

In this section, the energy consumption of the hardware of the IoMT-mote prototype is presented. Measurements were performed using a custom current sensing system based on the shunt resistor method. The shunt resistor method comprised sensing a current by measuring voltage drop along a small resistor, i.e., the shunt resistor, connected in series between the power supply and the load, i.e., the device under test (DUT). By dividing the voltage drop by the value of the shunt resistor, I=V/R, the current flowing through the resistor, and thus the current drawn by the DUT, was obtained. FIG. 11 shows a diagram of the measurement setup. In this setup, the voltage drop was measured using two analog inputs of the Saleae Logic Pro 8 logic analyzer to capture voltages at the two ends of a 1Ω shunt resistor. The voltage measures, sampled at 12.5 MHz, were saved on a host computer and exported to Matlab for processing; the voltage drop was obtained as the difference between the two voltage measures, and the current flowing through the 1Ω shunt resistor was equal to the voltage difference. Power was supplied by a DC supply, Instek GPS-4303.

MCU Power Consumption.

In Table II, the current and power consumption of the MCU is reported in different operation modes measured using the EEMBC energy measuring tool. Header J10 on the FRDM-KL03Z provided a convenient test point for measuring the MCU energy consumption. Specifically, the device was considered in RUN and WAIT modes both at 48 MHz and 3 MHz, in STOP, very-low-power stop (VLPS) mode and very-low-leakage (VLL0) mode. Power measures were obtained multiplying the current measures for the voltage supply, 3.3V.

TABLE II

Current and Power consumption of the MCU in different states.

| State | Current (mA) | Power (mW) |
|---|---|---|
| RUN @ 48 MHz | 6.6 | 21.78 |
| WAIT @ 48 MHz | 2.9 | 9.57 |
| RUN @ 3 MHz | 1.8 | 5.4 |

TABLE II-continued

Current and Power consumption of the MCU in different states.

| State | Current (mA) | Power (mW) |
|---|---|---|
| WAIT @ 3 MHz | 1.2 | 3.6 |
| STOP | 0.16 | 0.528 |
| VLPS | 0.005 | 0.0165 |
| VLLS0 | <0.001 | <0.003 |

In RUN mode the MCU operated at its maximum performance and consumed around 6.6 mA at 48 MHz. Every time there no tasks were scheduled, μTasker switched automatically to a low-power mode. By default, the MCU went into WAIT mode where all the peripherals function while the core is in Sleep mode, reducing the current drawn to 1 to 1.4 mA. As soon as a task was scheduled, an internal interrupt brought the MCU back to RUN mode. When less processing power was needed in RUN mode, e.g., when the MCU just read and stored sensed information, the clock frequency could be reduced to lower the power consumption. For example, the MCU drew 1.8 mA and 1 mA when underclocking the system to 3 MHz in RUN and WAIT mode, respectively. In STOP mode, the MCU went to deep sleep and all the peripheral clocks were stopped and the chip went static state bringing the current drawn down to 160 μA. In VLPS mode more peripherals were put to sleep and the current drawn was further reduced to 2.2 μA. Finally, in very-low-leakage stop (VLLS0) mode, all the peripheral including the RAM were shut off, bringing the current drawn down to less than the measurement sensitivity 1 μA.

FPGA Power and Resource Consumption.

Table III reports the current and power consumption of the different logic modules implemented on the FPGA measured using the shunt-resistor measuring system. The ICE40 Ultra evaluation board offered shunt resistors test point (TP) for measuring the current consumption of the FPGA core $I_{CC}$, as well as the FPGA I/O pins $I_{CCIO}$. Specifically, $I_{CC}$ was measured across the 1Ω series resistor R38 (TP10 and TP11). $I_{CCIO}$ was obtained as the sum of the current consumption of the three banks of I/O, which can be measured across the 1Ω series resistor R14 (TP1 and TP2), R96 (TP8 and TP9) and R96 (TP3 and TP4). Table III also compares the measured code and I/O pin currents with the estimated ones $\hat{I}_{CC}$ and $\hat{I}_{CCIO}$, obtained using the power estimator software tool offered by Lattice Semiconductor.

The current consumption for the SPI slave module (MCU interface), transmitter logic processing, the SPI master module (ADC interface), and the receiver logic processing were isolated. Power measures were obtained multiplying the current measures for the voltage supply, 1.2 V for the FPGA core and 3.3 V for the I/O pins The SPI Slave module consumed around 0.3 mA, and it was activated only for a short period of time during configuration of the PHY layer parameter and the exchange of byte between the FPGA and the MCU before transmitting, and after receiving a packet. The transmitter logic, which received data from the MCU and transformed bits into waveforms, consumed around 0.6 mA for processing, plus 1 mA of $I_{CCIO}$ when transmitting at the maximum transmission power, i.e., around 5 dBm. The SPI Master, running at 72 MHz to interface the FPGA with the ADC, consumed around 1.5 mA when active. The receiver logic operations, which comprised packet detection, synchronization, and bit decoding, consumed around 0.8 mA. The overall receiver logic consumption was about 2.3 mA during receiving operations.

TABLE III

Current and power consumption of hardware components for Tx, Rx and Idle state

| Module | $I_{cc}$ (mA) | $I_{ccio}$ (mA) | $I_{tot}$ (mA) | $P_{tot}$ (mW) |
|---|---|---|---|---|
| SPI Slave | 0.3 | 0 | 0.3 | 0.4 |
| Tx Logic | 0.6 | 1 | 1.6 | 4 |
| SPI Master | 0.7 | 0.8 | 1.5 | 3.5 |
| Rx Logic | 0.8 | 0 | 0.8 | 1 |
| Tot Tx | 0.6 | 1 | 1.6 | 4 |
| Tot Rx | 1.5 | 0.3 | 2.3 | 4.4 |

Total Power Consumption.

Table IV reports the current and power consumption of the IoMT-mote, considering the MCU, the FPGA, the ADC, and the receiver preamplifier. The MCU running a 3 MHz was considered, and the node was considered to be in Tx or Rx mode. The Tx logic was assumed to turn off when receiving, and the Rx logic when transmitting through clock gating. The transmitter power consumption reported in the table assume 5 dBm transmission power. Varying the transmission power from −25 dBm to 5 dBm, the transmitter consumed between 2.4 mA and 3.4 mA. The receiver consumed around 9.1 mA, including the MCU, FPGA, ADC and preamplifier consumption. Without preamplifier, the receiver current consumption went down to around 6.1 mA.

TABLE IV

Current and power consumption of hardware components for Tx and Rx states

| Component | Current (mA) | | Power (mW) | |
|---|---|---|---|---|
| | Tx | Rx | Tx | Rx |
| MCU | 1.8 | 1.8 | 6 | 6 |
| FPGA | 1.6 | 2.3 | 4 | 4.4 |
| ADC | — | 2 | — | 6.6 |
| Preamp | — | 3 | — | 9 |
| Tot. | 3.4 | 9.1 | 10 | 26 |

Active power consumption during receiving and transmitting operations was reduced by replacing the FPGA with an application-specific integrated circuit (ASIC). While it is hard to estimate the energy gain from replacing an FPGA with an ASIC, because FPGAs have a very wide range of very different internal architectures that result in non-linear relationship with ASICs, some studies suggest that the power reduction can be tenfold. As a drawback, using an ASIC loses the advantages of the FPGA, such as flexibility, time-to-market, and upgrades-in-the-field. In idle mode, the MCU current in VLLS1 was assumed to be 0.6 μA, while all the other component were shut down, as discussed in Section II-B2.

Table V compares the IoMT-mote prototype current and power consumption with the consumption of the TI CC2650 BLE MCU and the Microsemi ZL70103 transceiver that operate in the MICS band. For a fair comparison, the ZL70103 transceiver was considered as being controlled by a KL03 MCU running a 3 MHz; therefore the power consumption reported in Table V also includes the MCU power consumption. The MCU of the IoMT-mote prototype running a 3 MHz was considered, and the Rx current consumption was shown with and without preamplifier. The three devices were assumed as operating with 5 dBm transmission power. It was observed that the IoMT prototype hardware consumption was comparable with the consumption of commercial wireless devices.

TABLE V

Current and power consumption of the IoMT-mote prototype hardware compared to the TI CC2650 and ZL70103 consumption in Tx and Rx mode.

| | $I_{Tx}$ (mA) | $I_{Rx}$ (mA) | $P_{Tx}$ (mW) | $P_{Rx}$ (mW) |
|---|---|---|---|---|
| IoMT-mote | 3.4 | 6.1/9.1 | 10 | 17/26 |
| CC2650 | 10.47 | 6.47 | 34.5 | 22.3 |
| ZL70103 | 7.6 | 6.8 | 23.3 | 20.9 |

These results suggest that ultrasonic waves can be efficiently generated and received using low-energy and miniaturized components, supporting the feasibility of miniaturizing the IoMT platform described herein. Moreover, the comparison with RF-based systems suggests that the IoMT-mote can achieve comparable power consumption with commercial devices.

Example 2: Propagation Loss

Figure 12:
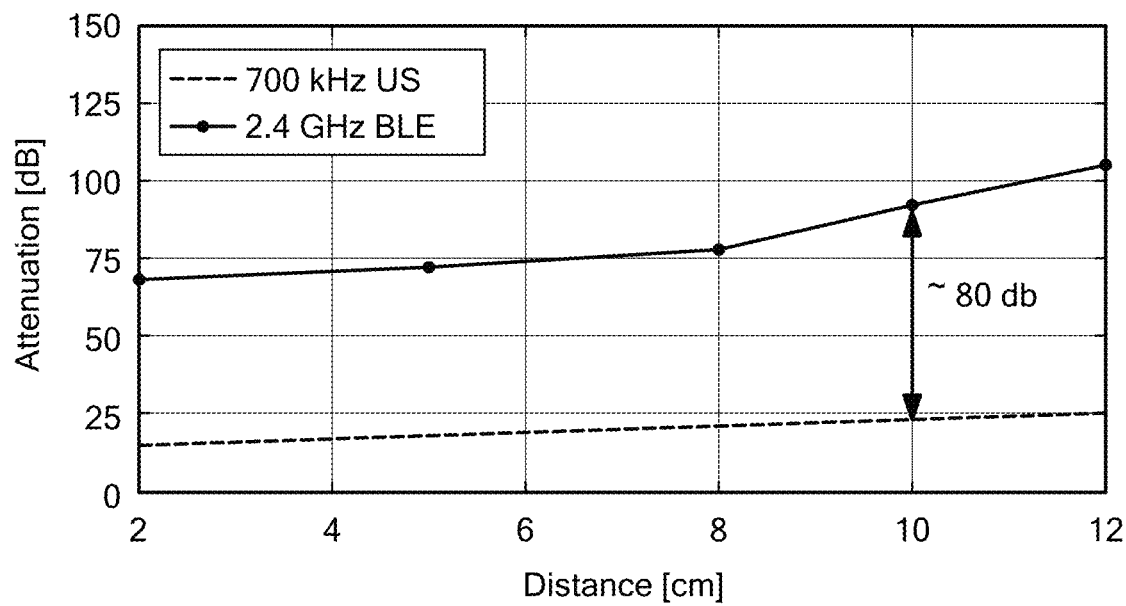
FIG. 12 is a graph of attenuation in pork meat for 2.4 GHz RF, and for 700 kHz ultrasonic waves as a function of propagation distance.
Figure 13:
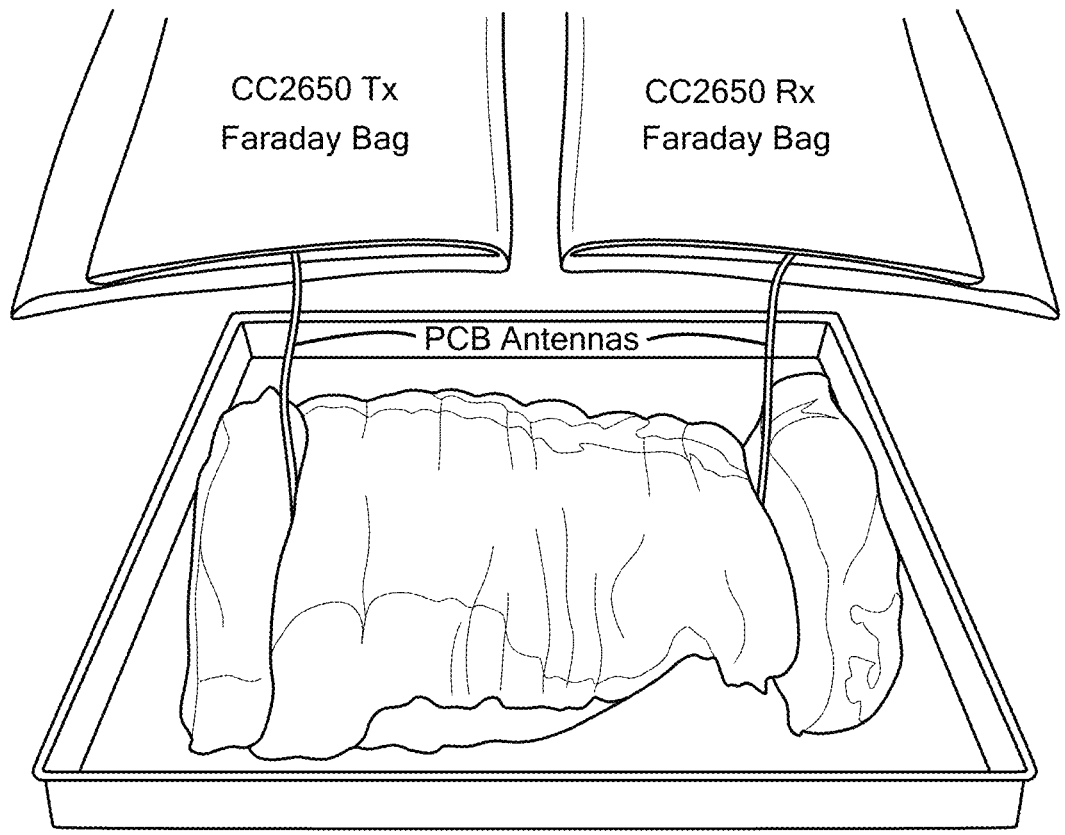
FIG. 13 is an illustration of an example of a measurement setup for a CC2650 device through pork meat using Faraday bags.

FIG. 12 shows attenuation loss in pork meat for RF waves at 2.4 GHz and for ultrasonic waves at 700 kHz. The attenuation included absorption by tissue, conversion losses and spread losses. Measurements were performed by gradually increasing the amount of pork meat between the transmitting and receiving antenna, or transducer. For the RF measurements, the received power was measured by the CC2650 MCU, while for the ultrasonic measurements prototype, the received power was measured using the Saleae Logic Pro 8 logic analyzer. To avoid RF leakages that can affect the measurement results, the two CC2650 boards were enclosed inside two Faraday shielding bags to attenuate up to 82 dB the RF leakage and therefore reduce the undesired effect of in-air RF propagation. FIG. 13 shows an example of the RF measurement setup. It was observed that for 2 to 12 cm propagation distance, RF attenuation was 55 to 80 dB higher than the ultrasonic attenuation.

Example 3: Bit-Error-Rate Evaluation

Figure 14:
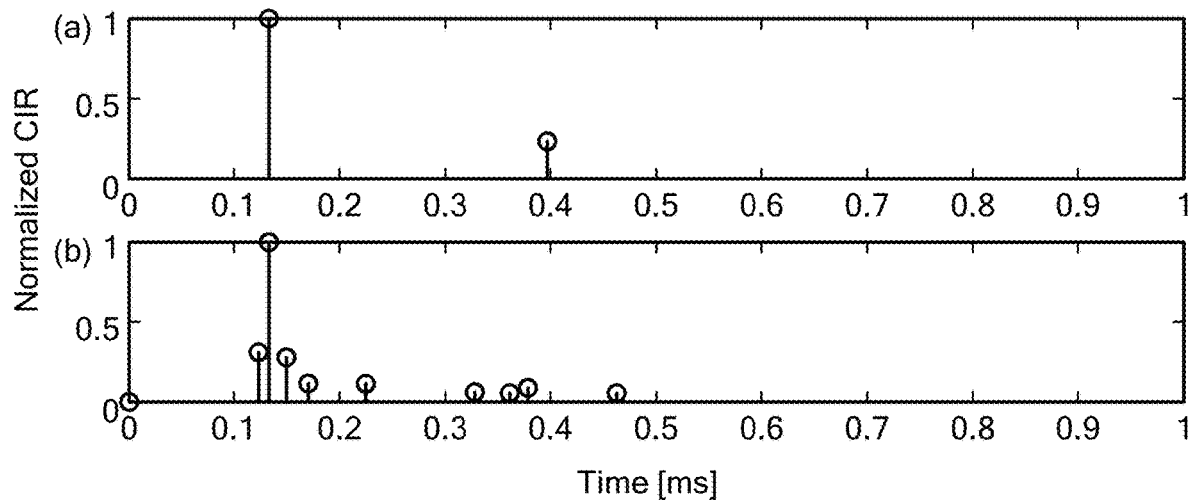
FIG. 14 is a graph of ultrasonic channel impulse response for (a) upper arm phantom and (b) thoracic phantom.

This example describes the performance the UsWB transmission scheme implementation on the IoMT-mote in terms of bit-error-rate as a function of the transmission power in different use-case scenarios. Ultrasonic phantoms were used that matched the acoustic properties of different human tissues, e.g., soft tissues, bones, and fluids. Specifically, an upper arm phantom and a thoracic phantom were used. The upper arm phantom emulated muscle tissue containing veins with fluid simulating blood. The thoracic phantom included the mid thoracic spinal segment containing spinal fluid, muscle, skin and other soft tissues. FIG. 14 shows the channel impulse response (CIR) of the two considered scenarios. The point at time=0 ms indicates the instant of transmission; the other points represent the time of arrival of the signal paths. It was observed that in the upper arm phantom almost no multipath effect was experienced, except for a secondary path caused by the reflection of the transmitted signal between the surfaces, which in fact require exactly 3 propagation time to arrive at the receiver. Because of the soft/hard tissue interface in the thoracic phantom, multipath effect was evidently stronger.

In these tests, the transmission power was varied, by connecting different attenuators between the FPGA output pin and the transmitter transducer. 1-pad attenuators implemented using purely resistive components that operate as simple voltage divider circuit were used. By using the attenuators, the transmission power was varied from 5 dBm (3 mW) to −25 dBm (3 μW). For each BER measurement up to 2500 packets of 48 bytes were transmitted, i.e., approximately 768 kilobits, containing pseudorandom-generated raw data. This allowed the detection of bit error rates in the order of $10^{-6}$. Two different hardware setups were also considered, one that included the AD8338 preamplifier and one that did not. In both cases, the received signal passed through the signal conditioning circuit based on the TI OPA835.

Upper Arm Phantom.

Figure 15:
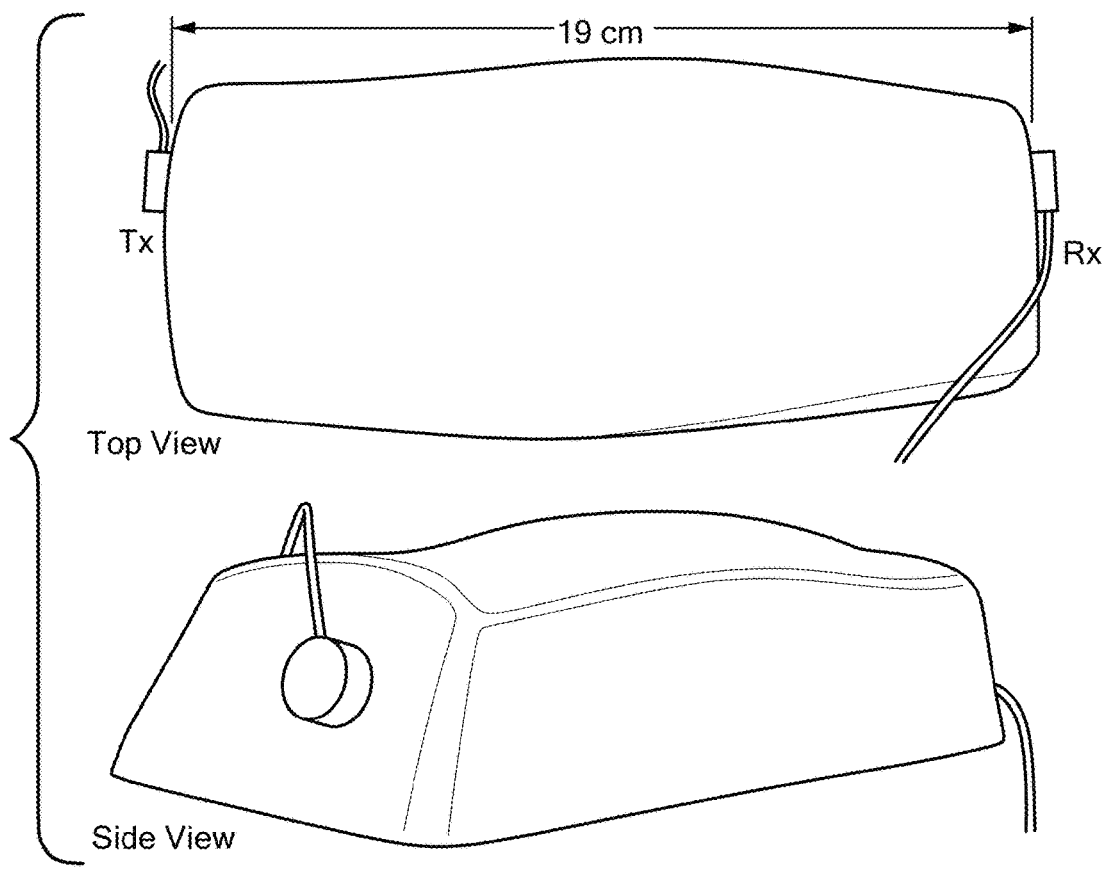
FIG. 15 is an illustration of an experiment setup employing an upper arm phantom.

For these tests, the two transducers were placed facing each other on the opposite surface of the upper arm phantom along the longest dimension, i.e., 19 cm. Mechanical coupling between the transducers and the phantom was achieved applying a water-based gel between the surfaces. The overall path loss between the transmitter and receiver was around 50 dB. The path loss included conversion loss of the two transducers, i.e., 12 dB, attenuation due to the tissue absorption and interface between tissue and fluid, and coupling loss cause by non-ideal impedance matching between the transducer surface and the phantom. FIG. 15 shows the setup for this set of experiments.

Figure 16:
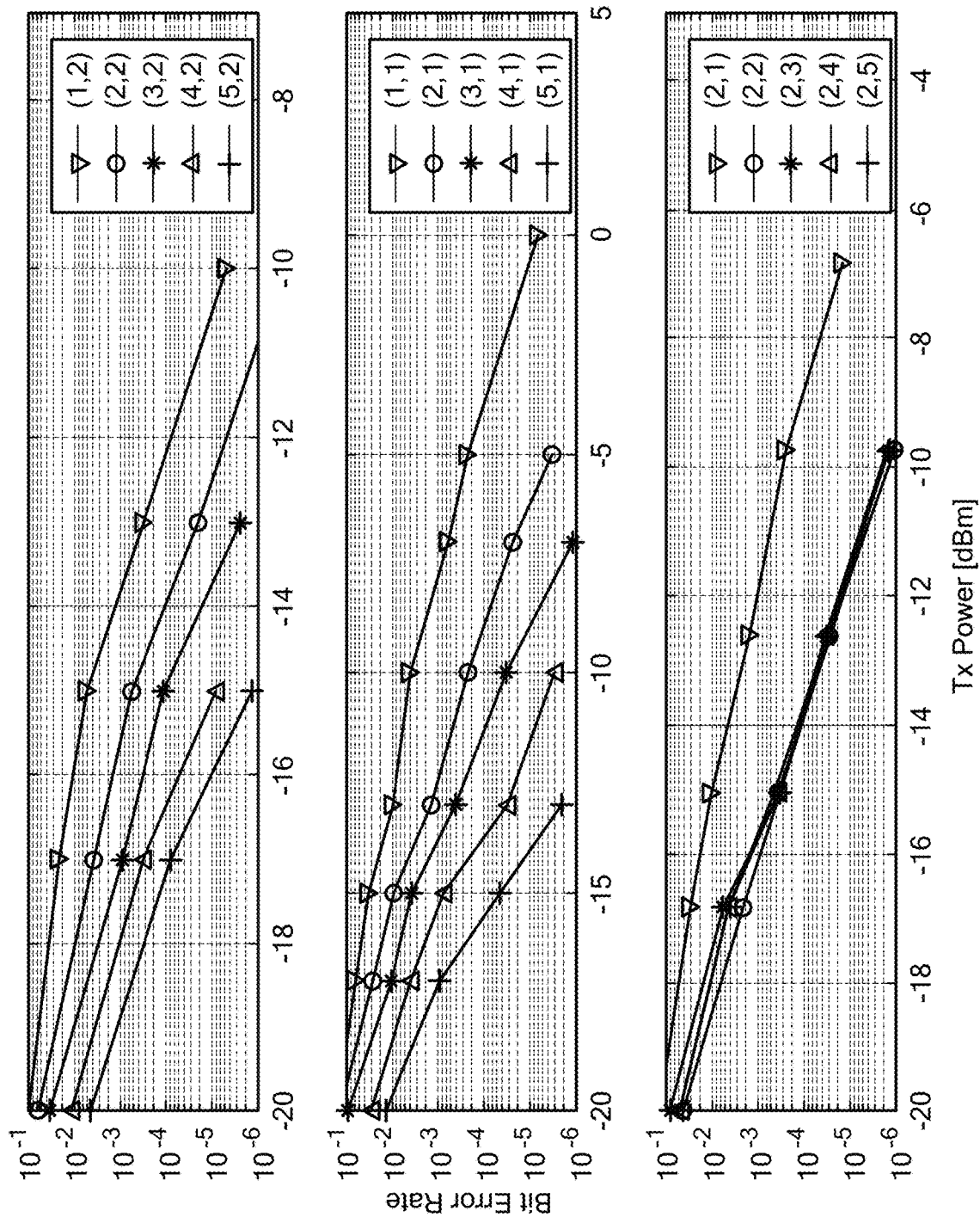
FIG. 16 is a graph of BER as a function of the transmission power (dBm) for a no-amp scenario in the upper arm phantom for code length in {1, 2, 3, 4, 5} and frame length equal to 2 (top) and 1 (center), and for frame length in {1, 2, 3, 4, 5} and code length equal to 2 (bottom)

FIG. 16 shows the BER as a function of the transmission power, for code length varying in {1,2,3,4,5} and frame length equal to 1 (center) and 2 (top), when no preamplifier was used. In this setup, there was very little noise measured at the receiver, and the system was limited by the receiver sensitivity. Without preamplifier, the receiver sensitivity was limited by the ADC resolution, which set the sensitivity of −62 dBV. A transmission power of −17 dBm gave a received voltage of −61 dBV, which was basically at the limit of the system sensitivity. If the transmission power were further decreased, the received signal would go below the receiver sensitivity, and become so distorted that synchronization failed and BER was very high. From these plots, it can be observed that the BER is a decreasing function of the SNR, and that the pseudo-random spreading code scheme mitigated the signal distortion, thus lowering the channel errors. However, increasing the code lengths decreased the data rate.

Increasing the frame length should not decrease the BER, since the multipath effect was limited and there were no interfering nodes in the channel. However, it was observed that changing the frame length from 1 to 2 lowered the BER. This happened because the frame increase reduced the effects of inter-symbol interference (ISI) of pulses overlapping with pulses in the consecutive time slot caused by the bandwidth limitation of the transducers. To further investigate this phenomenon, in FIG. 16 (bottom) the BER was plotted as a function of the SNR for frame length varying in {1,2,3,4,5} and code length equal to 2. It was observed, as expected, that increasing the frame length gave no advantage in terms of BER, except for the step 1-2, where the ISI effect caused by the transducers was predominant.

In the considered setup, the prototype achieved 90 kbit/s, with code length equals to 1 and frame length equals to 2, i.e., pair (1,2) with a $10^{-6}$ BER with an input power at the Tx transducer of about −10 dBm (0.1 mW). A data rate up to about 180 kbit/s could be achieved (also with $10^{-6}$ BER) with a (1,1) pair increasing the input power to 0 dBm (1 mW). Lower-power transmissions were also possible by compensating with longer spreading code. For example, in the current implementation, for a Tx power of −15 dBm (30

μW), and with a code length of 5 and frame length of 2, a data rate of 18 kbit/s was obtained with a BER lower than $10^{-6}$. Longer codes could be used for lower data rate and lower power transmissions, e.g., current implementation allowed up to code length 15 that led to a data rate of 6 kbit/s with frame length equal to 2. However, without using a preamplifier at the receiver, the minimum transmission power achievable was limited by the receiver sensitivity of −62 dBV.

Thoracic Phantom.

Figure 17:
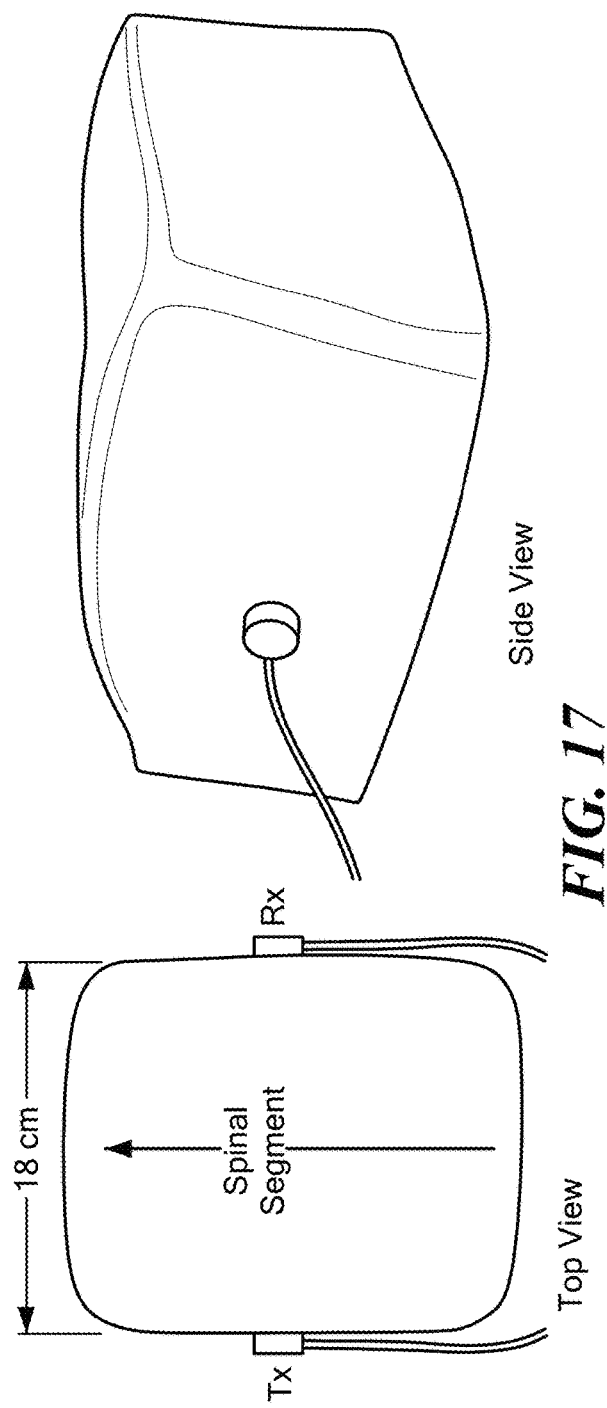
FIG. 17 is an illustration of an experiment setup for a thoracic phantom.

Because of the spinal segment, with this phantom the system communication performance through heterogeneous soft/hard tissue medium could be tested. For these tests, the two transducers were placed facing each other, 19 cm apart. The overall path loss between the transmitter and receiver was around 60 dB. The additional 10 dB loss compared to the upper arm setup was given by the higher attenuation due to the bone tissue, as well as the interface between soft/hard tissue and cerebral spinal fluid. For this set of experiments the preamplifier setup was used. FIG. 17 shows the setup for this set of experiments.

Figure 18:
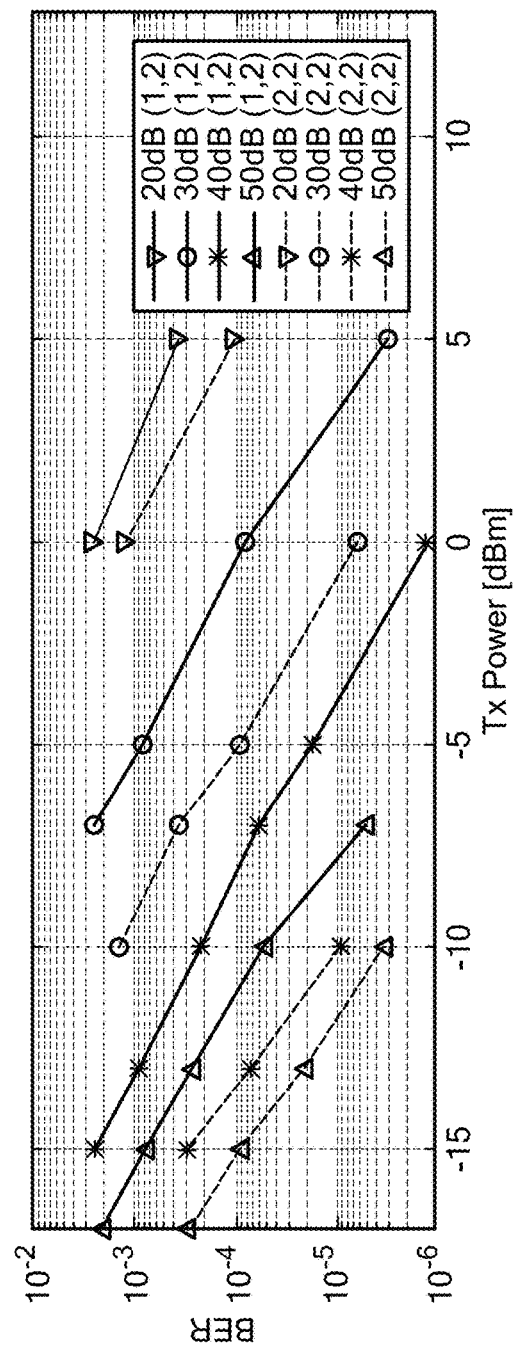
FIG. 18 is a graph of BER as a function of the transmission power in the thoracic phantom for code and frame length equal to 2 and different value of amplification gain at the receiver.

FIG. 18 shows the BER as a function of the transmission power for frame equal to 2, code length equal to 1 and 2, for different value of amplification gain at the receiver. FIG. 18 (bottom) compares these BER curves to the BER curves obtained in the 0-gain scenario when no preamplifier is used. We observe that an increase of 10 dBm in transmission power was needed to achieve the same BER performance of the upper arm scenario. This was because of the higher path loss as well as the higher multipath effect, as shown in FIG. 14. Again, at least a 40 dB gain was required for the preamplifier setup to outperform the no-amplifier setup. Moreover, because of the higher attenuation caused by the bone, without preamplifier a BER could only be achieved on the order of $10^{-5}$ with a pair (1,2), i.e., 90 kbit/s data rate, and with a transmission power of 5 dBm. In order to lower the BER, or to further increase the data rate to 180 kbit/s with pair (1,1), higher transmission power was needed. On the other hand, using the preamplifier with 40 dB gain and 50 dB gain, 90 kbit/s with $10^{-6}$ BER was achievable with 0 dBm and −8 dBm transmission power, respectively.

Whether to use the preamplifier or not depends on the application scenario considered, and it should account for other design requirements. Without the preamplifier, the 3 mA current that powers the preamplifier could be used to get an additional 10 dBm of the transmission power at the transmitter. Without using the preamplifier and increasing the transmission power, the power consumption could be balanced between the transmitter and receiver, which can be useful for energy fairness and network lifetime. Also, without the preamplifier, the size and the complexity of the design can be reduced, which can be another consideration for the system. On the other hand, using the 3 mA for the preamplifier can provide up to 60 dB gain at the receiver and drastically lower the transmission power.

Example 4: BLE v. UsWB

Packet-Error-Rate (PER).

Figure 19:
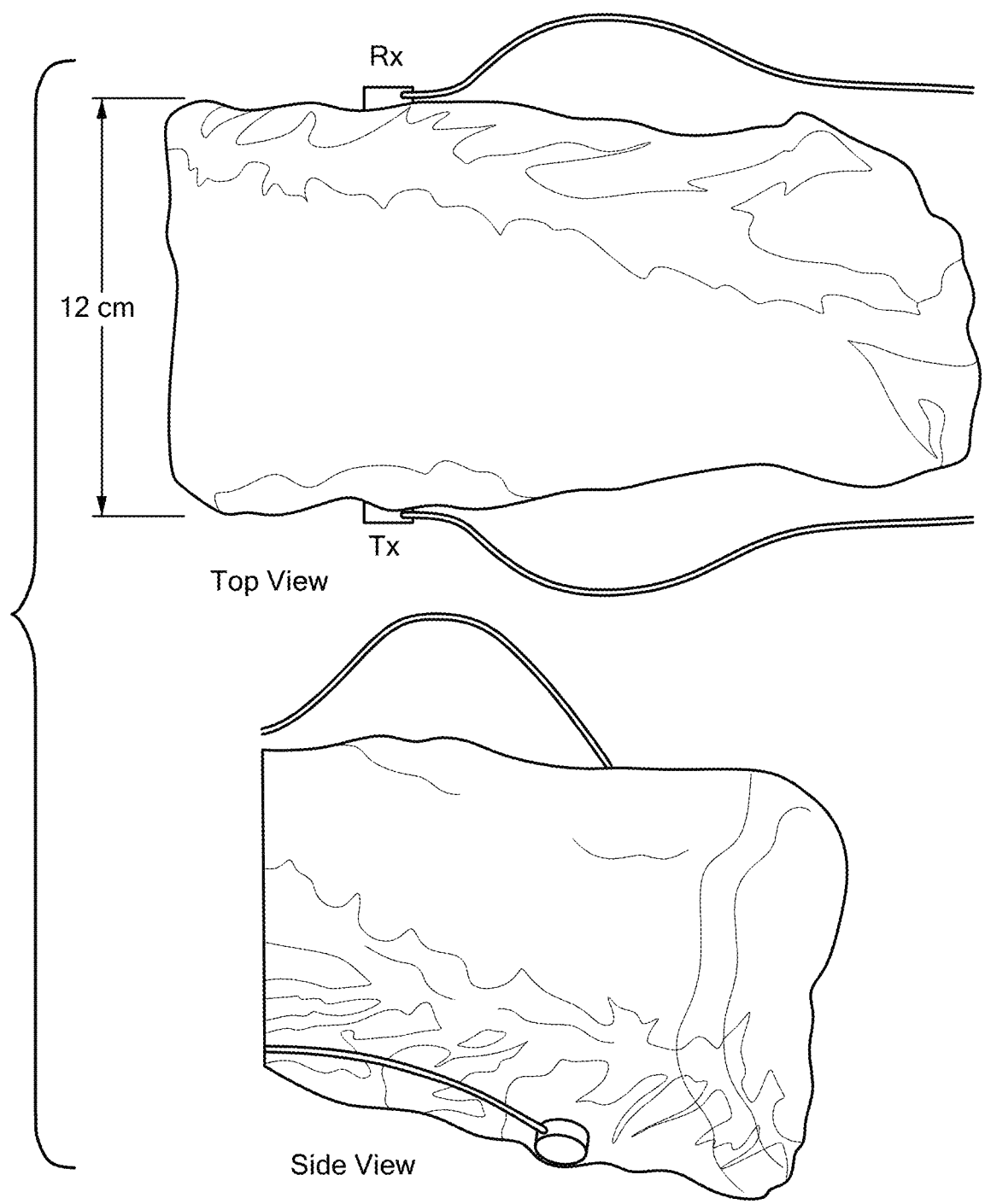
FIG. 19 is an illustration of an experiment setup for pork meat scenario along 12 cm.
Figure 20:
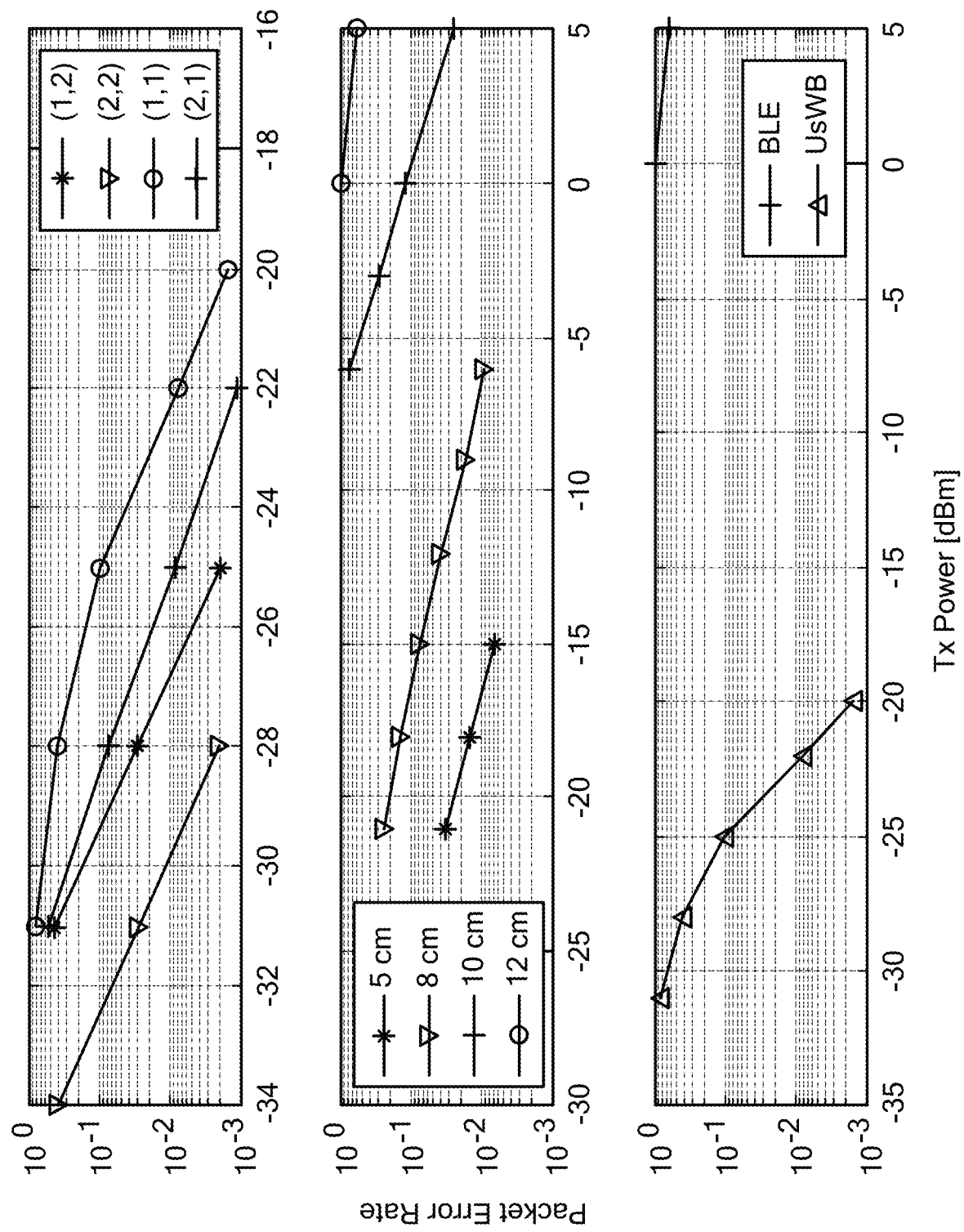
FIG. 20 is graph of PER for UsWB as a function of the transmission power in the 12 cm meat setup for code and frame length in {1,2} (top); PER of BLE in pork meat as a function of the transmission power for different communication distances (center); PER of BLE and UsWB (code and frame length equal to 1) as a function of the transmission power in 12 cm pork meat (bottom)

UsWB transmission scheme implemented in the IoMT-mote was compared with the BLE physical layer based on a 1 Mbit/s Gaussian frequency shift key (GFSK) implemented on the TI CC2650 in terms of reliability (PER) through pork meat. Pork meat closely emulates human muscular tissues and allowed the testing of both ultrasonic and RF-based communication side by side and evaluation of their performance in terms of reliability and energy consumption. For the IoMT-mote evaluation, a setup was considered where ultrasonic transducers were facing each other 12 cm apart, as shown in FIG. 19. For these experiments, a 50 dB gain was set at the receiver preamplifier. For the BLE evaluation, the TI SmartRF software tool was used to evaluate the PER performance of a BLE communication between two CC2650 BLE devices by transmitting 1000 32-bytes packet. The PER was obtained as the ratio between the number of packets received with errors, or not received at all, and the total number of packets transmitted. FIG. 20 (top) shows the UsWB PER as a function of the transmission power (dBm), for code and frame length in {1,2}. For $10^{-6}$ BER, the prototype achieved 180 kbit/s, pair (1,1), with code and frame length equal to 1, with a transmission power of about −20 dBm (10 μW). By using frame length equals to 2 to get rid of the ISI effect, a 90 kbit/s data rate was achieved, with the same $10^{-6}$ BER constraint, and transmission power of −27 dBm (2 μW). FIG. 20 (center) shows the PER performance of BLE in pork meat as a function of the transmission power for different communication distances. It can be observed that for longer distances higher transmission power was required, and for distances longer than 10 cm, reliability performance dropped dramatically. Specifically, for 12 cm distance, the PER became as high as 80% with the maximum transmission power available, i.e., 5 dBm, making communication almost unfeasible. With higher distances, the communication was completely disrupted, i.e., 100% PER.

In FIG. 20 (bottom), PER performance of BLE over a 12 cm distance was compared with the IoMT-mote performance (code and frame length equals to 1). It was observed that BLE required around 35 dBm higher transmission power to achieve the same reliability of UsWB. This gap can be further increased by implementing stronger synchronization and decoding operations in the UsWB PHY implementation. The lower transmission power, together with the lower absorption in tissues compared to RF strongly reduced any potential thermal effect caused by the increase of body temperature that could determine adverse effects.

Energy per Bit and Device Lifetime.

A remote monitoring application was considered in which a 20-byte information packet must be sent at least every minute between two devices. Specifically, a master node wanted to retrieve the information data from a slave node. 20-byte was selected because it was the maximum amount of application layer data that BLE allowed to be transmitted in a single LL packet. The energy consumption of the IoMT-mote was compared with the energy consumption of the CC2650 BLE devices. Current and power consumption values were assumed as reported in Table V, considering the IoMT-prototype. Energy per bit, Eb, was defined as the ratio between the total energy spent by the two devices for exchanging information data over the amount of successfully exchanged information data, and it was measured in J/bit. Network lifetime was the minimum between the master and slave's battery lifetime and it was measured in years.

For the BLE devices, a scenario was considered where the slave node initiated an advertising event every advertising interval $T_a$ using the three control channels sequentially. The master node connected, and the connection stayed open with a connection event happening every 32 s, i.e., the maximum connection interval available. In the following, it was assumed both devices were operating at 5 dBm transmission power, unless otherwise specified. Based on this scenario, the BLE devices consumed around 123 μJ for a data exchange, and therefore the energy per bit is equal to 0.77

μJ/bit. The IoMT-motes consumed around 57.4 μJ for each data exchange, and therefore the energy per bit is equal to 0.37 μJ/bit.

To evaluate the two systems in terms of device lifetime, transmitting, receiving, processing and idle states only were considered. Processing state occurred before and after a packet transmission and reception, and 0.5 ms interval with a consumption of 3 mA was assumed. 2 μA idle current consumption, and a 300 mAh battery were also assumed. Under these conditions, the BLE network lifetime was 12.5, against 14.8 years achieved by the UsWB. Note that these results were based on the hardware consumption and the LL protocol operations only. In the following, it is shown how these results were affected when considering the propagation and reliability characteristics of the two systems.

Figure 21:
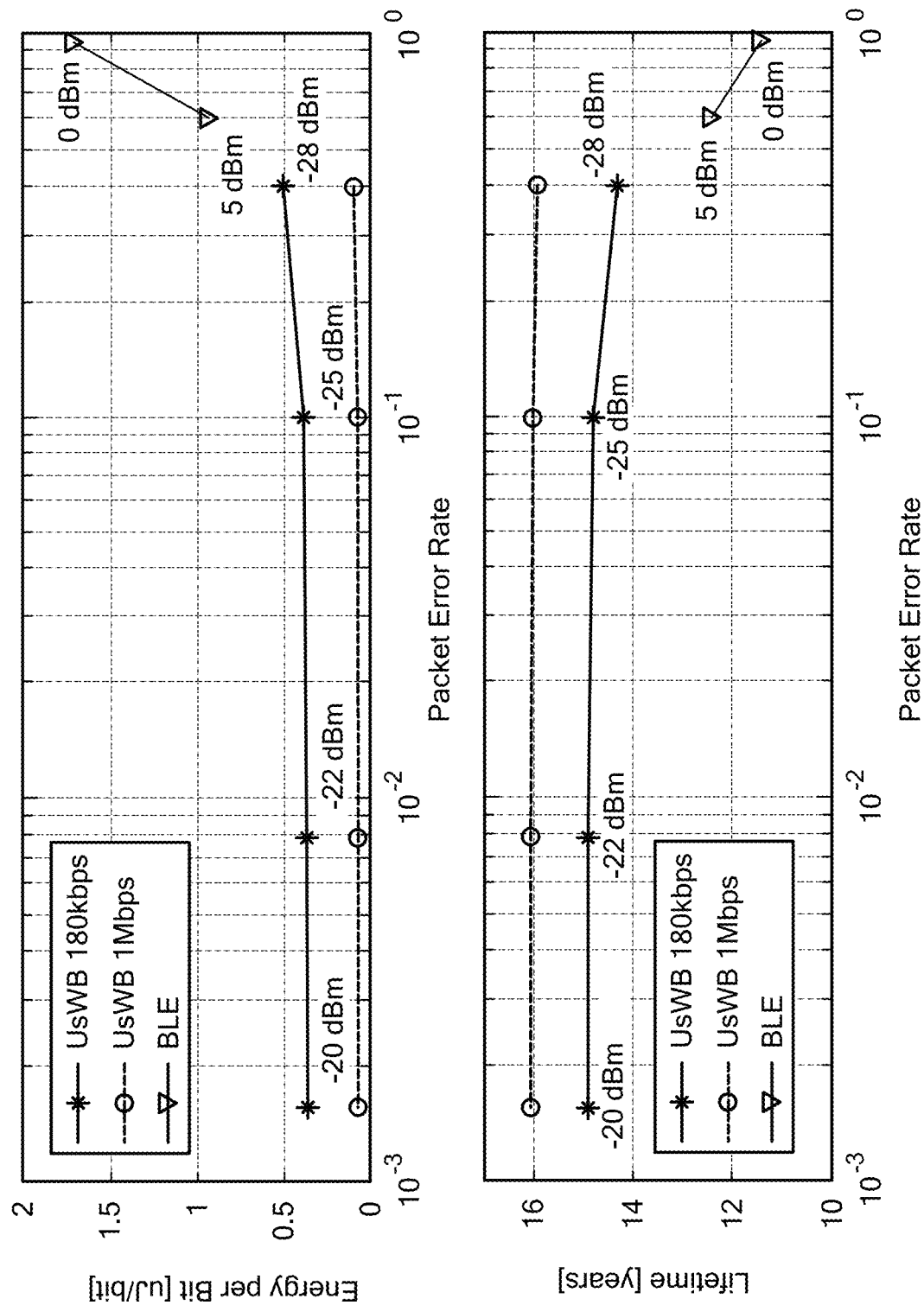
FIG. 21 is a graph of UsWB and BLE energy per bit (top) and network lifetime (bottom) as a function of the BER (left); UsWB and BLE energy per bit (top) and network lifetime (bottom) as a function of the BER in 12 cm of pork meat (right)

FIG. 21 shows the energy per bit (top) and the network lifetime (bottom) using the PER values obtained from the experiments discussed above. It can be observed how over 12 cm UsWB outperformed BLE in terms of lifetime and energy per bit. In fact, UsWB can achieve much lower PER with lower transmission power, and therefore keep the energy per bit and network lifetime close to the ideal values of 14.8 years achieved when BER is ideally zero. On the other hand, BLE can only operate over 12 cm at the maximum transmission power, still underperforming in terms of BER compared to UsWB. This further reduces the network lifetime and increase the energy cost for transmitting an information bit. Specifically, UsWB allows almost two more years of operations while achieving much higher reliability than BLE, i.e., about three order of magnitude lower PER. FIG. 21 shows how the UsWB energy per bit and lifetime performance would scale if the data rate were increased from 180 kbit/s to 1 Mbit/s to match the BLE data rate. This can be achieved using ultrasonic transducers with higher bandwidth and/or using higher order modulation schemes. Results show how energy per bit can become as low as 0.07 μJ/bit and network lifetime increase up to 16 years.

As used herein, "consisting essentially of" allows the inclusion of materials or steps that do not materially affect the basic and novel characteristics of the claim. Any recitation herein of the term "comprising," particularly in a description of components of a composition or in a description of elements of a device, can be exchanged with "consisting essentially of" or "consisting of."

It will be appreciated that the various features of the embodiments described herein can be combined in a variety of ways. For example, a feature described in conjunction with one embodiment may be included in another embodiment even if not explicitly described in conjunction with that embodiment.

To the extent that the appended claims have been drafted without multiple dependencies, this has been done only to accommodate formal requirements in jurisdictions which do not allow such multiple dependencies. It should be noted that all possible combinations of features which would be implied by rendering the claims multiply dependent are explicitly envisaged and should be considered part of the invention.

The present invention has been described in conjunction with certain preferred embodiments. It is to be understood that the invention is not limited to the exact details of construction, operation, exact materials or embodiments shown and described, and that various modifications, substitutions of equivalents, alterations to the compositions, and other changes to the embodiments disclosed herein will be apparent to one of skill in the art.

What is claimed is:

1. A method of controlling a plurality of networked medical devices, the method comprising the steps of:
   (a) providing a system comprising:
      an RF/ultrasound communication device;
      one or more ultrasound communication devices implantable within a body and capable of ultrasound communication with the RF/ultrasound communication device, each of the ultrasound communication devices comprising:
         a communication unit comprising an ultrasonic transceiver to transmit and receive ultrasonic signals, the communication unit configured to transmit and receive the ultrasonic signals through biological tissue to and from communication units of other implanted or wearable medical devices in the network of devices, and
         a processing unit in communication with the communication unit, the processing unit including a core unit comprising:
            a logic device including a physical layer of a protocol stack, and
            a controller unit including upper layers of the protocol stack, the upper layers including at least a link layer and an application layer, the controller unit further including a data processing module at the application layer for communication with a sensor or actuator,
         wherein the link layer is connected with the logic device to send parameters to the physical layer for transmission of ultrasonic signals through the biological tissue and with the data processing module to transfer data or parameters to or from the sensor or actuator, and
         wherein the processing unit further comprises an energy management module operative to adjust power usage based on operating requirements by automatically sending signals to wake-up, power up, shut down electronic components, to adjust at runtime a core clock frequency according to processing power required, and to select at runtime a low-power mode; and
      one or more sensing devices and/or one or more actuating devices, each in communication with one of the ultrasound communication devices of the system;
   (b) configuring the protocol stack and logic device of each ultrasound communication device in the system;
   (c) acquiring data from the one or more sensing devices and optionally processing the data;
   (d) optionally communicating the data using the RF/ultrasound communication device, an access point, and the internet to a physician;
   (e) optionally receiving reprogramming instructions using the RF/ultrasound communication device, access point, and internet;
   (f) optionally reconfiguring the protocol stack and logic device of one or more selected ultrasound communication devices in the system in response to the reprogramming instructions; and
   (g) optionally causing one or more of said actuating devices to change their actuation state.

2. An ultrasound communication device for transmitting signals ultrasonically within a network of implanted and/or wearable medical devices, comprising:
   a communication unit comprising an ultrasonic transceiver to transmit and receive ultrasonic signals, the communication unit configured to transmit and receive the ultrasonic signals through biological tissue to and from other communication units of other implanted or wearable medical devices in the network of devices; and a processing unit in communication with the communication unit, the processing unit including a core unit comprising:
- a logic device including a physical layer of a protocol stack, and
- a controller unit including upper layers of the protocol stack, the upper layers including at least a link layer and an application layer, the controller unit further including a data processing module at the application layer for communication with a sensor or actuator,
- wherein the link layer is connected with the logic device to send parameters to the physical layer for transmission of ultrasonic signals through the biological tissue and with the data processing module to transfer data or parameters to or from the sensor or actuator; and wherein the processing unit further comprises an energy management module operative to adjust power usage based on operating requirements by automatically sending signals to wake-up, power up, shut down electronic components, to adjust at runtime a core clock frequency according to processing power required, and to select at runtime a low-power mode.

3. The device of claim 2, wherein the reconfigurable logic device further comprises transmitter chain blocks to output a train of pulses following a predefined time-hopping pattern and receiver chain blocks to decode ultrasonic transmissions received from the communication unit and deliver a stream of binary data to the controller unit.

4. The device of claim 2, wherein the reconfigurable logic device includes a register module operative to store configuration parameters received from the controller unit and to route the configuration parameters to one or more modules within the reconfigurable logic device, the configuration parameters including one or more of a spreading code, a spreading code length, a time-hopping frame length, a time-hopping sequence, a packet payload size, or a length of a preamble.

5. The device of claim 2, wherein the reconfigurable logic device includes a configurable serial peripheral interface (SPI) module in communication with the controller unit.

6. The device of claim 5, wherein the SPI module is operative to configure communication settings, including one or more of data rate, clock polarity and clock phase.

7. The device of claim 5, wherein the SPI module is operative to enable communication with the processor or a peripheral device.

8. The device of claim 5, wherein the SPI module includes a master module in communication with the processor and a slave module.

9. The device of claim 5, wherein the SPI module is operative to trigger sampling operations on an analog to digital converter and to read back sampled digital waveforms.

10. The device of claim 2, wherein the reconfigurable logic device includes a field-programmable gate array, a masked-programmed gate array, an application specific integrated circuit, a small-scale integrated circuit, a programmable logic array, or a programmable logic device.

11. The device of claim 2, further comprising a sensing or actuating unit, and wherein the controller unit is operative in real time to trigger a reading from the sensing or actuating unit and to process the reading and is further operative to transmit data processed from the reading to the reconfigurable logic device for transmission as an ultrasonic signal.

12. The device of claim 2, wherein the core unit is operative to reconfigure one or more of the application layer, the link layer, a media access control layer, and a network transport layer of the protocol stack.

13. The device of claim 2, further comprising a sensor interface to enable connection between the processing unit and a sensor device or an actuating device.

14. The device of claim 2 in communication with a sensing device selected from the group consisting of a motion sensor, a gyroscope, an accelerometer, a cardiac rhythm monitor, a heart rate monitor, a pulse monitor, a blood pressure monitor, a glucose sensor, a drug pump monitor, a sleep sensor, a REM sleep duration sensor, a still camera, a video camera, a sensor for one or more biomolecules, a sensor for one or more pharmaceutical agents or pharmaceutical formulation ingredients, a sensor for a dissolved gas or ion, a sensor for pH, a sensor for ionic strength, and a sensor for osmolality.

15. The device of claim 2 in communication with an actuating device selected from the group consisting of a drug pump, a heart stimulator, a heart pacemaker, a bone growth stimulator, a deep brain stimulator, a neurostimulator, and a neuromuscular electrical stimulator.

16. The device of claim 2, wherein the device is implantable within a body or wearable on a skin surface of a body.

17. The device of claim 2, wherein the communication unit further includes a radio frequency (RF) interface operative to receive and transmit in-air RF transmissions, and wherein the device is wearable on a skin surface of a body.

18. The device of claim 17, wherein the device is in communication via said RF transmissions with a further device coupled to a communications network.

19. The device of claim 18, further comprising a wireless controller is operative connect to a Bluetooth Low Energy (BLE) access point device and/or to a 6LoWPAN device.

20. The device of claim 18, wherein the wireless controller includes a Message Queue Telemetry Transport (MQTT) client module that is operative to read data from the implantable device through the ultrasonic interface, publish sensor readings to an MQTT broker, open a connection with the MQTT broker through an IPv6 address, authenticate an application, and/or publish new content.

21. A system comprising:
an RF/ultrasound communication device; and
one or more ultrasound communication devices of claim 2 implantable within a body and capable of ultrasound communication with the RF/ultrasound communication device.

* * * * *